US011253616B2

(12) United States Patent
Farwell et al.

(10) Patent No.: US 11,253,616 B2
(45) Date of Patent: Feb. 22, 2022

(54) SMALL MOLECULES FOR DUAL FUNCTION POSITRON EMISSION TOMOGRAPHY (PET) AND CELL SUICIDE SWITCHES

(71) Applicant: THE TRUSTEES OF THE UNIVERSITY OF PENNSYLVANIA, Philadelphia, PA (US)

(72) Inventors: Michael Farwell, Wynnewood, PA (US); Mark Sellmyer, Philadelphia, PA (US); Katheryn M. Lohith, Lansdale, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 700 days.

(21) Appl. No.: 16/123,797

(22) Filed: Sep. 6, 2018

(65) Prior Publication Data

US 2019/0070321 A1 Mar. 7, 2019

Related U.S. Application Data

(60) Provisional application No. 62/554,699, filed on Sep. 6, 2017.

(51) Int. Cl.
| | |
|---|---|
| *A61K 51/04* | (2006.01) |
| *A61K 35/17* | (2015.01) |
| *A61K 31/506* | (2006.01) |
| *A61K 38/17* | (2006.01) |
| *C12N 9/22* | (2006.01) |
| *C12N 9/06* | (2006.01) |
| *G01N 33/50* | (2006.01) |
| *C12N 15/85* | (2006.01) |

(52) U.S. Cl.
CPC ........ *A61K 51/0459* (2013.01); *A61K 31/506* (2013.01); *A61K 35/17* (2013.01); *A61K 38/1774* (2013.01); *A61K 51/0463* (2013.01); *C12N 9/003* (2013.01); *C12N 9/22* (2013.01); *C12N 15/85* (2013.01); *C12Y 105/01003* (2013.01); *G01N 33/505* (2013.01); *C12N 2800/80* (2013.01)

(58) Field of Classification Search
CPC .. A61K 51/0459; A61K 35/17; A61K 31/506; A61K 38/1774; A61K 51/0463; C12N 2800/80; C12N 9/22; C12N 9/003; C12Y 105/01003
See application file for complete search history.

(56) References Cited

U.S. PATENT DOCUMENTS

| | | |
|---|---|---|
| 8,906,682 B2 | 12/2014 | Kalos et al. |
| 8,911,993 B2 | 12/2014 | Kalos et al. |
| 8,916,381 B1 | 12/2014 | Kalos et al. |
| 8,975,071 B1 | 3/2015 | Kalos et al. |
| 9,101,584 B2 | 8/2015 | Kalos et al. |
| 9,102,760 B2 | 8/2015 | Kalos et al. |
| 9,102,761 B2 | 8/2015 | Kalos et al. |
| 2014/0068797 A1 | 3/2014 | Doudna et al. |
| 2016/0272618 A1 | 9/2016 | Schwarz et al. |
| 2019/0070321 A1* | 3/2019 | Farwell .............. A61K 51/0459 |

OTHER PUBLICATIONS

Amara, et al., "A versatile synthetic dimerizer for the regulation of protein-protein interactions", Proc. Natl. Acad. Sci., 94(20), Sep. 1997, 10618-10623.
Banaszynski, et al., "Chemical control of protein stability and function in living animals", Nat. Med., 14(10), Oct. 2008, 1123-1127.
Bonger, et al., "Small molecule displacement of a cryptic degron causes conditional protein degradation", Nat. Chem. Biol., 7(8), Aug. 2011, 531-537.
Clackson, et al., "Redesigning an FKBP-ligand interface to generate chemical dimerizers with novel specificity", Proc. Natl. Acad. Sci, 95(18), Sep. 1998, 10437-10442.
Cohen, et al., "Suicide gene-mediated modulation of graft-versus-host disease.", Leuk Lymphoma. 34(5-6), Aug. 1999, 473-80.
Distasi, et al., "Inducible Apoptosis as a Safety Switch for Adoptive Cell Therapy", N. Engl. J. Med., 365(18), Nov. 2011, 1673-1683.
Sellmyer, et al., "Bacterial infection imaging with [18F]fluoropropyl-trimethoprim", Proc. Natl. Acad. Sci., 114, Aug. 2017, 8372-8377.
Sellmyer, et al., "Quantitative PET Reporter Gene Imaging with [11C]Trimethoprim", Mol. Ther., 25, Jan. 2017, 120-126.
Straathof, et al., "An inducible caspase 9 safety switch for T-cell therapy", Blood, 105, Jun. 2005, 4247-4254.
Tey, et al., "Inducible caspase 9 suicide gene to improve the safety of allodepleted T cells after haploidentical stem cell transplantation", Biol. Blood Marrow Transplant., 13, Aug. 2007, 913-924.

(Continued)

*Primary Examiner* — Tracy Vivlemore
*Assistant Examiner* — Ebenezer O Sackey
(74) *Attorney, Agent, or Firm* — Saul Ewing Arnstein & Lehr LLP; Kathryn Doyle; Justin Crotty

(57) ABSTRACT

The present invention includes an engineered cell comprising a chimeric antigen receptor (CAR) further comprising a nucleic acid molecule comprising a suicide gene comprising a ligand binding domain and a suicide domain wherein the ligand binding domain is capable of binding to radiolabeled tracer or a small molecule suicide switch. This invention also includes methods for inducing apoptosis of an engineered cell, methods for assessing the efficacy or toxicity of an adoptive cell therapy in a subject, methods for detecting the quantity of engineered T cells in a subject, methods for monitoring an immunotherapy treatment in a subject and methods of imaging engineered T cells in a subject. In some embodiments, the imaging is performed via Positron Emission Topography (PET). This invention further includes a chemical inducer of dimerization (CID), wherein the CID is a Bis-Trimethoprim (Bis-TMP).

1 Claim, 37 Drawing Sheets

Specification includes a Sequence Listing.

(56) References Cited

OTHER PUBLICATIONS

Thomis, et al., "A Fas-based suicide switch in human T cells for the treatment of graft-versus-host disease", Blood, 97(5), Mar. 2001, 1249-1257.
Yang, et al., "Investigating Protein-Ligand Interactions with a Mutant FKBP Possessing a Designed Specificity Pocket", J. Med. Chem., 43(6), Feb. 2000, 1135-1142.
Zhou, et al., "Long-term outcome after haploidentical stem cell transplant and infusion of T cells expressing the inducible caspase 9 safety transgene", Blood, 123(25), Jun. 2014, 3895-3905.

\* cited by examiner

Generation of pBMN-eDHFR-Casp9

1. Vector
   pBMN eDHFR-YFP

2. ΔCaspase9 insert from
   pMSCV-F-del Casp9.IRES.GFP 3. pBMN eDHFR-Casp9

Trimethoprim derivatives

Bis-TMP-33

Bis-TMP-27

Bis-TMP-21

Bis-TMP-16

Bis-TMP-10

Bis-TMP-8

Bis-TMP-6

Tris-TMP-7

SMALL MOLECULES FOR DUAL FUNCTION POSITRON EMISSION TOMOGRAPHY (PET) AND CELL SUICIDE SWITCHES

CROSS-REFERENCE TO RELATED APPLICATION

The present application is entitled to priority under 35 U.S.C. § 119(e) to U.S. Provisional Patent Application No. 62/554,699, filed Sep. 6, 2017 which is hereby incorporated by reference in its entirety herein.

SEQUENCE LISTING

The present application contains a Sequence Listing which has been submitted in ASCII format via EFS-Web and is hereby incorporated by reference in its entirety. Said ASCII copy, created on Sep. 6, 2018, is named 046483-7178US1-sequence-listing-Text.txt and is 577 kilobytes in size.

BACKGROUND OF THE INVENTION

The ability to follow the migration and distribution of biologically active cells in living organisms is crucial for both the development of cell-based therapies and for the elucidation of biological processes in basic research. Notably, T cells engineered with chimeric antigen receptors (CARs) that target tumor-associated antigens have shown dramatic activity in a variety of cancers, including advanced chemotherapy-resistant tumors previously considered to be incurable. However, a major obstacle in the development of CAR T cells that target solid tumors is the difficulty in assessing their treatment efficacy, antitumor effects, and therapy-related toxicities, since the fate of the therapeutically administered cells cannot be assessed directly. As a result, patients are typically evaluated based on indirect measures of response that are acquired months after initiation of treatment, such as changes in tumor size or serum tumor markers. Additionally, many times it is unclear if an adverse event is related to CAR T cell toxicity or other factors. Although serial sampling of solid tumors or biopsy of a potential site of toxicity is an option, it still has the potential for sample bias (both within a lesion and across the entire burden of disease), and it generally carries enough risk that it is not acceptable to patients or their physicians. Thus, in vivo cell-tracking methods are needed to noninvasively monitor the presence, distribution, quantity, and viability of the administered cells in target tumors or elsewhere in the body.

One approach to in vivo imaging of lymphocyte migration involves the transduction of cells with a reporter gene that can be visualized by a radiolabeled reporter probe. This technique has the advantage that the reporter gene is passed on to daughter cells, which results in amplification of the signal as the number of cells increases. This signal amplification is especially significant for CAR T cells, which have been shown to increase by 1,000- to 10,000-fold in patients treated for lymphoma. Additionally, a reporter gene allows cells to be interrogated at any time via injection of the appropriate imaging agent. This is particularly important for CAR T cells, since fever onset and peak cell proliferation typically occur around 2-3 weeks following adoptive transfer, and questions remain about the persistence of T cells months after treatment.

Many different reporter genes exist, including herpes simplex virus type 1 thymidine kinase (hsvTK), sodium iodide symporter (NIS), and human norepinephrine transporter (hNET), to name a few. However, all of these reporter genes have limitations; one of the major limitations of the existing reporter genes is that they are unable to function as a rapidly acting suicide gene or regulator of protein expression. Although some of the reporter genes have shown mild activity as a suicide gene, the majority have not, and a subset such as hsvTK are nonhuman in origin and highly immunogenic which largely precludes their clinical use. Since reporter genes generally require the addition of a receptor, transporter, or enzyme to the host cells, they have the potential to reduce the viability or efficacy of those cells, which limits their clinical application if they are only being employed for imaging.

Thus, there is a need in the art for a novel approach to in vivo cell tracking, which overcomes some of the limitations of the currently available reporter genes. This invention addresses this need and provides in vivo cell-tracking methods to noninvasively monitor the presence, distribution, quantity, and viability of the administered cells.

SUMMARY OF THE INVENTION

The present invention includes compositions and methods of using small molecules for dual function positron emission tomography (PET) imaging and cell suicide switches.

In one aspect, the invention includes an engineered cell comprising a chimeric antigen receptor (CAR) and further comprising a nucleic acid molecule comprising a suicide gene comprising a ligand binding domain and a suicide domain wherein the ligand binding domain is capable of binding to radiolabeled tracer or a small molecule suicide switch.

In one aspect, the invention includes a method of inducing apoptosis of an engineered cell. The method comprises introducing into the cell (a) a chimeric antigen receptor (CAR); (b) a nucleic acid molecule comprising a suicide gene; and (c) a ligand wherein the ligand comprises a dimerized Trimethoprim (TMP) that activates the suicide gene, thereby inducing apoptosis of the engineered cell.

In one aspect, the invention includes a method of assessing the efficacy or toxicity of an adoptive cell therapy in a subject. The method comprises (a) administering to the subject an engineered T cell comprising a chimeric antigen receptor (CAR) and a nucleic acid molecule comprising a suicide gene that comprises a ligand binding domain and a suicide domain; (b) administering to the subject a radiolabeled tracer capable of binding to the ligand binding domain; (c) detecting the amount of radiolabeled tracer bound by imaging; and, (d) assessing the efficacy or toxicity of the adoptive cell therapy in the subject. In one embodiment, when the adoptive cell therapy is assessed as toxic the radiolabeled tracer is replaced by a dimerized ligand capable of binding to the ligand binding domain and activating the suicide domain thereby inducing cell death of the engineered T cell. In another embodiment, the dimerized ligand comprises AP1903, AP20187 and Bis-TMP.

In one aspect, the invention includes a method of detecting the quantity of engineered T cells in a subject. The method comprises (a) administering to the subject an engineered T cell comprising a chimeric antigen receptor (CAR) and a nucleic acid molecule comprising a suicide gene that comprises a ligand binding domain and a suicide domain; (b) administering to the subject a radiolabeled tracer capable of binding to the ligand binding domain; and, (c) imaging the amount of radiolabeled tracer bound thereby detecting the quantity of engineered T cells in the subject.

In another aspect, the invention includes a method of monitoring an immunotherapy treatment in a subject. The method comprises (a) administering to the subject an engineered T cell comprising a chimeric antigen receptor (CAR) and a nucleic acid molecule comprising a suicide gene that comprises a ligand binding domain and a suicide domain; (b) administering to the subject a radiolabeled tracer capable of binding to the ligand binding domain; and, (c) detecting the level of radiolabeled tracer bound by imaging as a measure of the immunotherapy treatment. In one embodiment, the imaging is performed by positron emission tomography (PET).

In yet another aspect, the invention includes a method of imaging engineered T cells in a subject. The method comprises (a) administering to the subject an engineered T cell comprising a chimeric antigen receptor (CAR) and a nucleic acid molecule comprising a suicide gene that comprises a ligand binding domain and a suicide domain; (b) administering to the subject a radiolabeled tracer capable of binding to the ligand binding domain; and, (c) detecting the radiolabeled tracer by imaging using positron emission tomography (PET).

In still another aspect, the invention includes a composition comprising a chemical inducer of dimerization (CID), wherein the CID is a Bis-Trimethoprim (Bis-TMP) of the formula (I):

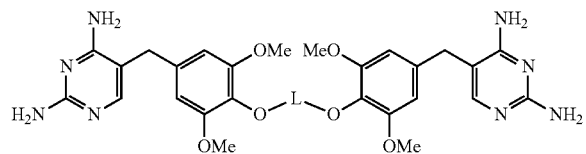

wherein L is a chemical linker having a length of about 1 to about 50 atoms.

In a further aspect, the invention includes a composition comprising a ligand of F36V-FKBP of formula (II):

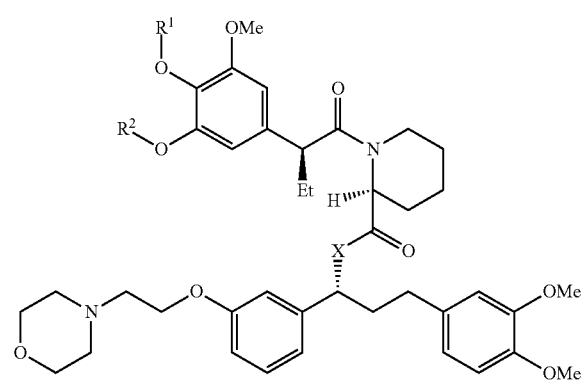

wherein X is NH or O; (a) $R^1$ is $CH_2Y$, $CH_2CH_2Y$, or $CH_2CH_2CH_2Y$ and $R^2$ is $CH_3$; or (b) $R^2$ is $CH_2Y$, $CH_2CH_2Y$, or $CH_2CH_2CH_2Y$ and $R^1$ is $CH_3$; and Y is F or $^{18}F$.

In one embodiment, the cell is a T cell.

In one embodiment, the suicide domain is an inducible caspase 9 (iCasp9) domain.

In one embodiment, the ligand binding domain is selected from the group consisting of FKBP, F36V-FKBP, and *E. coli* dihydrofolate reductase (eDHFR).

In one embodiment, the iCasp9 domain comprises *E. coli* dihydrofolate reductase (eDHFR) ligand binding domain (eDHFR-iCasp9).

In another embodiment, the eDHFR-iCasp9 further comprises a linker consisting of 15 or 18 amino acids in length.

In one embodiment, the radiolabeled tracer is selected from the group consisting of [$^{11}$C]-Shield-1; [$^{18}$F]-Shield-1; [$^{11}$C]-Trimethoprim ([$^{11}$C]-TMP) and [$^{18}$F]-Trimethoprim ([$^{18}$F]-TMP).

In another embodiment, the dimerized Trimethoprim is Bis-Trimethoprim (Bis-TMP) of the formula (I):

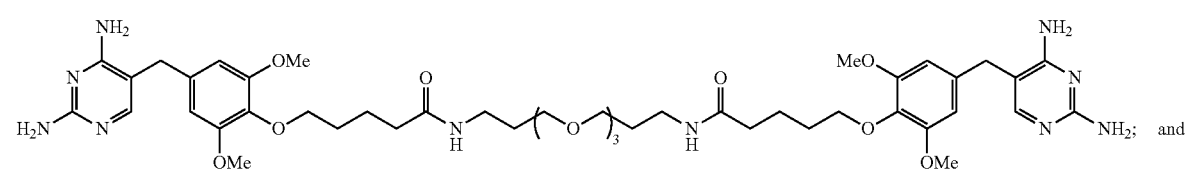

wherein L is a chemical linker having a length of about 1 to about 50 atoms.

In yet another embodiment, the Bis-TMP is a compound selected from the group consisting of:

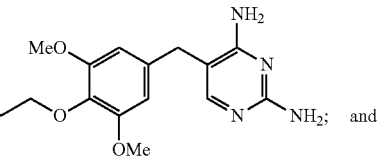

and

-continued

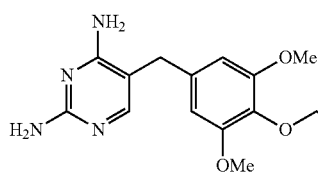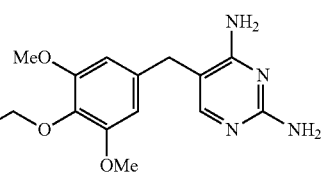

In one embodiment, the engineered T cell(s) is/are autologous to the subject.

In another embodiment, the engineered T cell(s) is/are allogenic to the subject.

In one embodiment, the subject is a mammal.

In another embodiment, the mammal is a human.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A: iCasp9 is based on human caspase 9, in which the recruitment domain of the caspase has been replaced by F36V-FKBP. This allows the caspase pathway to be activated by the small molecule AP1903, which is a dimer of Shield-1 that causes apoptosis via dimerization of the F36V-FKBP/caspase 9 fusion protein. FIG. 1B: The LID system is based on the addition of a degradation sequence (degron) to the C terminus of F36V-FKBP, which is then fused to a protein of interest. In the absence of Shield-1 the degron is bound to FKBP and the protein is stable. However, when Shield-1 is present, it binds tightly to FKBP, displaces the degron, and induces rapid degradation of the LID domain and the fused protein of interest.

FIG. 3A: HEK293 cell uptake studies with [$^{11}$C]TMP. FIG. 3B: Small animal PET/CT imaging of DHFR+ and DHFR− tumors with [$^{11}$C]TMP.

FIG. 4A: First route, compound A was synthesized as a mixture of enantiomers. FIG. 4B: Second route, stereoselective synthesis of compound A, which was then coupled to the secondary amine (synthesized as in the 1$^{st}$ route). No HPLC separation of diastereomers was needed.

FIG. 5A: Synthesis of [$^{11}$C]Shld1. FIG. 5B: HPLC analysis of [$^{11}$C]Shld1 compared with cold Shield-1 from Cheminpharma, LLC. FIG. 5C: Luminescence of HCT116 cells stably expressing L106P-tsLuc following treatment with cold Shield-1 (3 nM to 10 uM) and incubation with luciferin.

DETAILED DESCRIPTION

Definitions

Figure 1A:
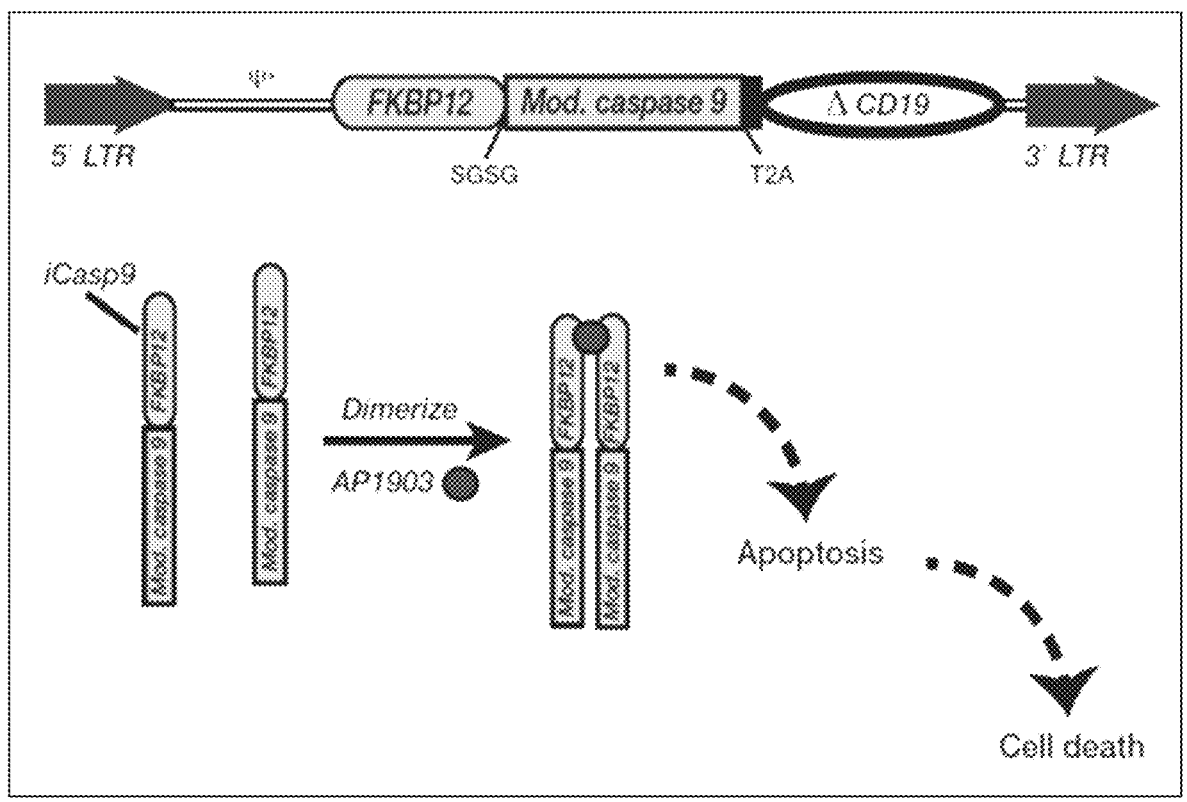
FIGS. 1A-1B are series of diagrams illustrating iCasp9 pathway and the ligand-induced degradation (LID) system.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies (scFv) and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. α and β light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

The term "chimeric antigen receptor" or "CAR," as used herein, refers to an artificial T cell receptor that is engineered to be expressed on an immune effector cell and specifically bind an antigen. CARs may be used as a therapy with adoptive cell transfer. T cells are removed from a patient and modified so that they express the receptors specific to a particular form of antigen. In some embodiments, the CARs has specificity to a selected target, for example a B cell surface receptor. CARs may also comprise an intracellular activation domain, a transmembrane domain and an extracellular domain comprising a tumor associated antigen binding region. In some aspects, CARs comprise an extracellular domain comprising an anti-B cell binding domain fused to CD3-zeta transmembrane and intracellular domain.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

The term "cleavage" refers to the breakage of covalent bonds, such as in the backbone of a nucleic acid molecule or the hydrolysis of peptide bonds. Cleavage can be initiated by a variety of methods, including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, fusion polypeptides may be used for targeting cleaved double-stranded DNA.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody can be replaced with other amino acid residues from the same side chain family and the altered antibody can be tested for the ability to bind antigens using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD30L, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via. RNA-guided DNA cleavage.

In the type II CRISPR/Cas system, short segments of foreign DNA, termed "spacers" are integrated within the CRISPR genomic loci and transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter. CRISPR/CAS mediated genome editing and regulation, highlighted its transformative potential for basic science, cellular engineering and therapeutics.

The term "CRISPRi" refers to a CRISPR system for sequence specific gene repression or inhibition of gene expression, such as at the transcriptional level.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "FK506 Binding Protein (FKBP)" refers to a family of proteins that have prolyl isomerase activity and are related to the cyclophilins in function, though not in amino acid sequence. FKBPs have been identified in many eukaryotes from yeast to humans and function as protein folding chaperones for proteins containing proline residues. FKBPs belong to the immunophilin family. In some embodiments, the FKBP is F36V-FKBP. In some embodiments, a dimerized ligand capable of binding FKBP is useful for the methods of this invention. In some embodiments, the dimerized ligand capable of binding FKBP refers to a compound represented by the structure:

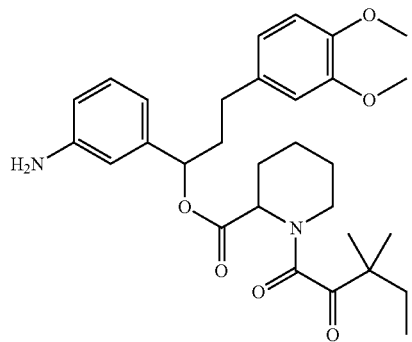 [SMILES: CCC(C)(C)C(=O)C(=O)N1CCCCC1C(=O)OC(CCc1ccc(OC)c(OC)c1)c1cccc(N)c1]

or any derivative or analog thereof.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Humanized" forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

"Fully human" refers to an immunoglobulin, such as an antibody, where the whole molecule is of human origin or consists of an amino acid sequence identical to a human form of the antibody.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

The term "imaging" as used herein refers to any method of scanning the body of a subject using techniques such as positron emission tomography (PET) or single photon emission computed tomography (SPECT), among others.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present invention to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

The term "knockdown" as used herein refers to a decrease in gene expression of one or more genes.

The term "knockout" as used herein refers to the ablation of gene expression of one or more genes.

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" as used herein, is meant a changed state or structure of a molecule or cell of the invention. Molecules may be modified in many ways, including chemically, structurally, and functionally. Cells may be modified through the introduction of nucleic acids.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the plasma membrane of a cell.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an MHC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "suicide gene" as used herein refers to a suicide or apoptosis-inducing gene operably linked to a promoter, which may be constitutive or inducible. Examples of a suicide gene include, but are not limited to, a herpes simplex virus thymidine kinase (HSV-TK), the cytoplasmic domain of Fas, a caspase such as caspase-8 or caspase-9, cytosine deaminase, E1A, FHIT, and other known suicide or apoptosis-inducing genes. The suicide gene comprises a ligand binding domain and a suicide domain.

The term "suicide gene product" as used herein refers to the expression product of the suicide gene.

The term "suicide domain" as used herein means that portion of the suicide gene that when activated induces DNA cleavage, generally leading to apoptosis of a cell in which the suicide domain resides.

A "ligand binding domain" as used herein means a domain that binds a ligand, for example a radiolabeled tracer or a small molecule suicide switch.

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

One aspect of this invention includes an engineered cell comprising a chimeric antigen receptor (CAR) and further comprising a nucleic acid comprising a suicide gene comprising a ligand binding domain and a suicide domain wherein the ligand binding domain is capable of binding to radiolabeled tracer or a small molecule suicide switch.

The invention contemplates use of any cell known in the art that can be genetically modified. In some embodiments, the genetically engineering cell is a T-cell, NK-cell, macrophage, B-cell, stem cell, hematopoietic stem cell, mesenchymal stem cell, neuroprogenitor cell, induced pluripotent cell, or any combination thereof.

Other aspects of this invention includes methods for inducing apoptosis of an engineered cell, methods for assessing the efficacy or toxicity of an adoptive cell therapy in a subject, methods for detecting the quantity of engineered T cells in a subject, methods for monitoring an immunotherapy treatment in a subject and methods of imaging engineered T cells in a subject.

In some embodiments, the methods of the invention comprise administering to the subject an engineered T cell comprising a chimeric antigen receptor (CAR) and a nucleic acid molecule comprising a suicide gene that comprises a ligand binding domain and a suicide domain, administering to the subject a radiolabeled tracer capable of binding to the ligand binding domain; and, detecting the amount of radiolabeled tracer bound by imaging.

In some embodiments, the imaging is performed via Positron Emission Topography (PET).

In other embodiments, the efficacy or toxicity of the adoptive cell therapy in the subject is assessed and continuation, modification or termination of the therapy is recommended. In some embodiments, when adoptive cell therapy is assessed as toxic the radiolabeled tracer is replaced by a cold (non radiolabeled) dimerized ligand capable of binding to the ligand binding domain and activating the suicide domain thereby inducing cell death of the engineered T cells.

In some embodiments, the radiolabeled tracer is a radiolabeled monomeric or a dimeric compound. In some embodiments, the radiolabeled tracer is a radiolabeled monomer. In some embodiments, the radiolabeled tracer is selected from the group consisting of [$^{11}$C]-Shield-1, [$^{18}$F]-Shield-1, or any radiolabeled derivative known in the art capable of binding to FKBP (such as F36V-FKBP). In other embodiments, the radiolabeled tracer is a monomer or a dimer selected from the group consisting of [$^{11}$C]-Trimethoprim ([$^{11}$C]-TMP) and [$^{18}$F]-Trimethoprim ([$^{18}$F]-TMP), or any radiolabeled derivative known in the art capable of binding to dihydrofolate reductase (DHFR).

In some embodiments, the radiolabeled tracer is administered to the subject at very low concentrations, so its occupies 1-5% of the available target receptors. In some embodiments, the administered radiolabeled tracer does not have a measurable physiological effect on the subject.

The radiolabeled tracer compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, 3H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In certain embodiments, isotopically labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}$C, $^{18}$F, $^{15}$O and $^{13}$N, is useful in Positron Emission Topography (PET) studies for examining target protein concentration and/or substrate receptor occupancy. Isotopically-labeled compounds are prepared by any suitable method or by processes using an appropriate isotopically-labeled reagent in place of the non-labeled reagent otherwise employed.

Another aspect of this invention includes a chemical inducer of dimerization (CID) wherein the CID is a dimerized ligand capable of binding to the ligand binding domain of the suicide gene and activating it thereby inducing cell death.

In certain embodiments, the CID is a Bis-Trimethoprim (Bis-TMP) of Formula (I), or a salt, solvate, enantiomer, diastereoisomer or tautomer thereof:

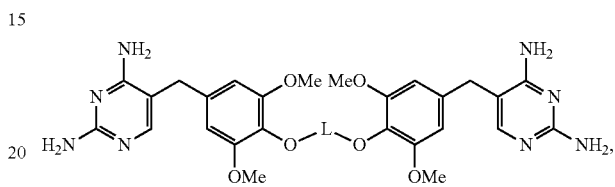

wherein L is a chemical linker having a length of about 1 to about 50 atoms.

In certain embodiments, L is an alkylene, heteroalkylene, alkenylene, heteroalkenylene, alkynylene, or heteroalkynylene. In other embodiments L has a backbone consisting of about 31 atoms. In other embodiments L has a backbone consisting of 25 atoms. In yet other embodiments L has a backbone consisting of 19 atoms. In yet other embodiments L has a backbone consisting of 14 atoms.

In certain embodiments, L is a linker selected from the group consisting of:

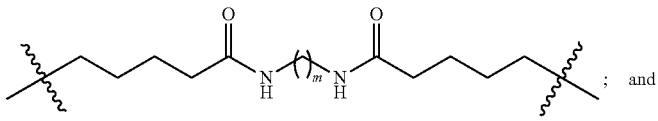

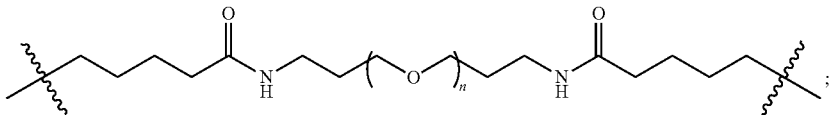

wherein k is an integer from 1-50, m is an integer from 1-38 and n is an integer from 1-11.

In certain embodiments, k is selected from the group consisting of 31, 25, 19 and 14. In other embodiments, m is selected from the group consisting of 19, 13, 7 and 2. In yet other embodiments, n is selected from the group consisting of 1, 3 and 5.

In certain embodiments, the Bis-TMP of Formula (I) is a compound selected from the group consisting of:

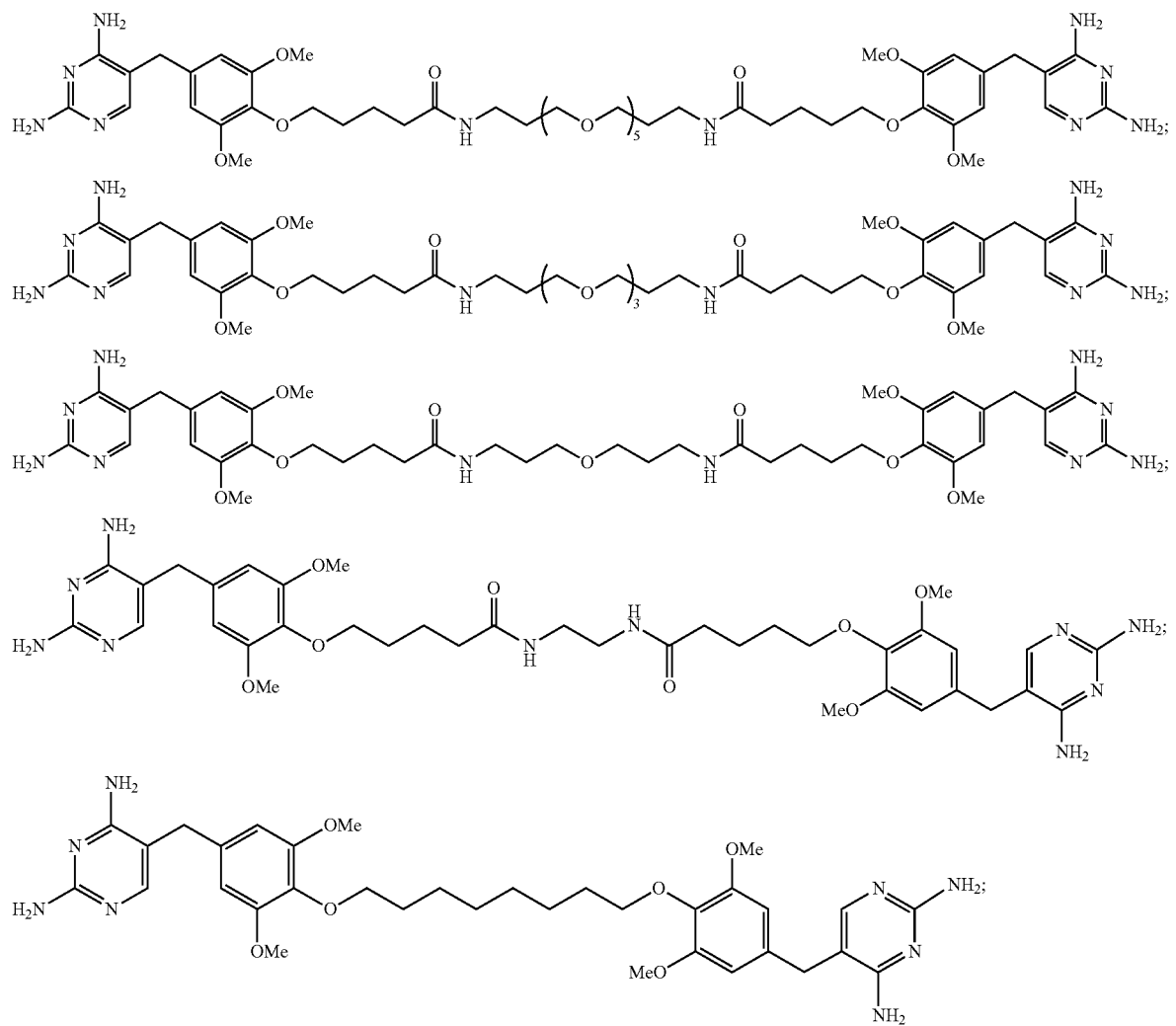
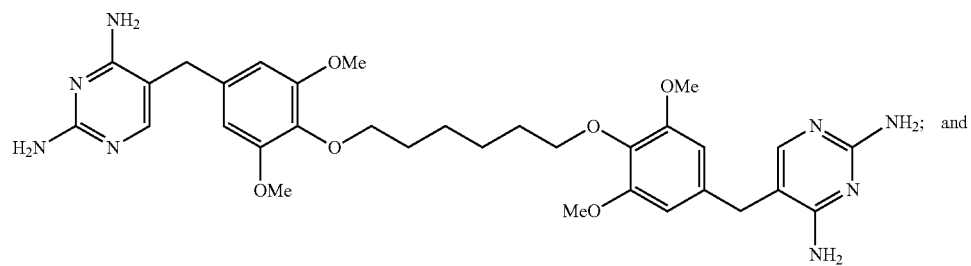
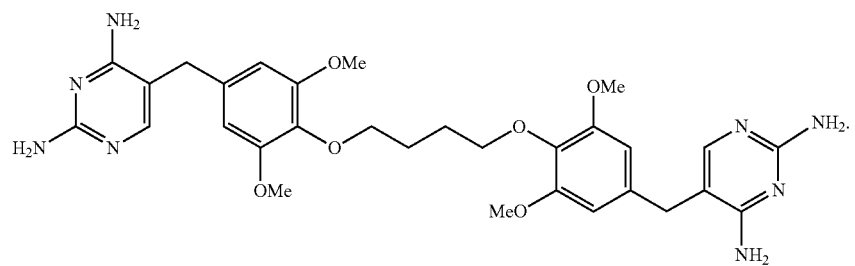

Another aspect of this invention includes an engineered cell comprising a chimeric antigen receptor (CAR) and further comprising a ligand-induced degradation (LID) system and a ligand wherein the ligand comprises a radiolabeled tracer. In some embodiments, a degradation sequence (degron) is fused to the C terminus of F36V-FKBP.

In one embodiment, the ligand of F36V-FKBP is a compound of formula (II):

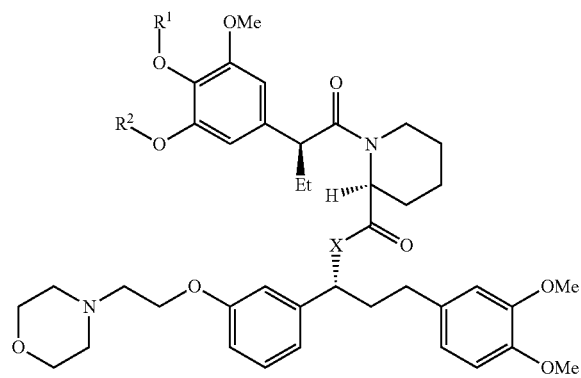

wherein
X is NH or O;
a) $R^1$ is $CH_2Y$, $CH_2CH_2Y$, or $CH_2CH_2CH_2Y$ and $R^2$ is $CH_3$; or
b) $R^2$ is $CH_2Y$, $CH_2CH_2Y$, or $CH_2CH_2CH_2Y$ and $R^1$ is $CH_3$; and
Y is F or $^{18}F$.

In other embodiments, the radiolabeled tracer is selected from the group consisting of [$^{11}$C]-Shield-1; [$^{18}$F]-Shield-1. In some embodiments, the radiolabeled tracer is replaced by a cold non radiolabeled ligand selected from the group consisting of Shield-1, AP1903 and AP20187, wherein the cold non radiolabeled ligand is capable of degrading the CAR.

Suicide Gene:

Some of the potential side effects of CAR T cells can be overcome by the co-expressing a suicide gene in the CART cell. In the present invention, a radiolabeled tracer is added to the engineered CAR T cells of the invention and these cells are then tracked in vivo, monitored and selectively removed in case toxicity arises in the subject or after targeting B cells for depletion when treating a disease or condition.

The methods of the invention include use of an isolated nucleic acid comprising a suicide gene. Examples of suicide genes include, but are not limited to, herpes simplex virus thymidine kinase (HSV-TK), the cytoplasmic domain of Fas, a caspase such as caspase-8 or caspase-9, cytosine deaminase, E1A, FHIT, and other known suicide or apoptosis-inducing genes (Straathof et al., 2005, Blood 105: 4247-4254; Cohen et al., 1999, Leuk. Lymphoma 34:473-480; Thomis et al., 2001, Blood 97:1249-1257; Tey et al., 2007, Biol. Blood Marrow Transplant 13:913-924; and Di Stasi et al., 2011, N. Engl. J. Med. 365:1673-1683).

The suicide gene may be operably linked to a promoter, such as an inducible promoter sequence. Examples of inducible promoters include, but are not limited to, a heat shock promoter, a tetracycline-regulated promoter, a steroid-regulated promoter, a metal-regulated promoter, an estrogen receptor-regulated promoter, and others known in the art. In one aspect, the invention includes an isolated nucleic acid sequence comprising a nucleic acid sequence comprising a suicide gene and a nucleic acid encoding a chimeric antigen receptor. In another aspect, the invention includes an isolated nucleic acid sequence comprising a suicide gene and a nucleic acid encoding a chimeric antigen receptor.

In one embodiment, the suicide gene is under the control of an inducible promoter.

In yet another embodiment the suicide domain is an inducible caspase 9 (iCasp9) domain.

In some embodiments, the suicide gene is in an expression vector. In an exemplary embodiment, the present invention includes a vector comprising a nucleic acid sequence comprising a suicide gene. The expression vector may also include other genes, such as a chimeric antigen receptor and/or CRISPR system disclosed elsewhere herein.

The invention also includes a cell comprising the suicide gene. In an exemplary aspect, the present invention includes a modified cell comprising a nucleic acid comprising a suicide gene and a nucleic acid encoding a chimeric antigen receptor.

In one embodiment, the CAR modified T cell comprises nucleic acids encoding a suicide gene as a separate nucleic acid sequence from the CAR construct. For example, HSV-TK, iCasp9, the cytoplasmic domain of Fas, or a caspase can be incorporated into genetically engineered T cells separate from the CAR construct. In another embodiment, the CAR modified T cell comprises a suicide gene in the same construct as the nucleic acids encoding the CAR. In this embodiment, the nucleic acid comprising the suicide gene may be upstream or downstream of the nucleic acid encoding the CAR.

In one embodiment, expression of the suicide gene is activated in the cell by contacting the cell with an inducing agent administered to the cell or to a subject comprising the cell. The inducing agent then activates an inducible promoter to express the suicide gene. In such an embodiment, the inducing agent is administered to the subject to induce expression of the suicide gene.

In one embodiment, the suicide binding domain comprises a ligand binding domain selected from the group consisting of FKBP, F36V-FKBP, E. coli dihydrofolate reductase (eDHFR). eDHFR is a bacterial protein involved in DNA synthesis that is highly genetically conserved across many bacterial species. The eDHFR protein is a small, 159 residue, 18 kDa essential enzyme involved in DNA and amino acid synthesis in all living organisms that is often used in biochemical studies and protein engineering tools. In one embodiment, iCasp9 domain comprises eDHFR ligand binding domain (eDHFR-iCasp9). In another embodiment, eDHFR-iCasp9 further comprises a linker consisting of 15 or 18 amino acids in length. In some embodiments, the linker comprises Ser-Gly-Gly-Gly-Ser (SEQ ID NO: 1) amino acids motifs.

In another embodiment, the ligand is a monomer or a dimer radiolabeled tracer. In some embodiments, the radiolabeled tracer is a monomer that does not activate the suicide gene.

In one embodiment, the radiolabeled tracer is selected from the group consisting of [$^{11}$C]-Shield-1; [$^{18}$F]-Shield-1; [$^{11}$C]-Trimethoprim ([$^{11}$C]-TMP) and [$^{18}$F]-Trimethoprim ([$^{18}$F]-TMP). Shield-1 is a monomer with high affinity for F36V-FKP domain. TMP is a small molecule antibiotic routinely used in the clinic that has high affinity and specificity for the eDHFR (see for instance US patent application US2016/0272618 incorporated herein by reference in its entirety). As a monomer, TMP also does not activate the suicide gene iCasp9. Various TMP based radiolabeled tracers are described in US Patent application US2016/031600, incorporated herein by reference in its entirety. The radiolabeled tracer compounds listed herein are stabilizing compounds and do not trigger the activation of the suicide gene unless dimerized.

In some embodiments, a suicide gene product that is expressed from the suicide gene is activated by an activating agent, such as a dimerization agent. For example, the dimerization agents, such as AP1903 (rimiducid), AP20187 or any derivative or analog known in the art, promote dimerization and activation of caspase-9 molecules. In other instances, the dimerization agent is a chemical inducer of dimerization (CID) such as BIS-Trimethoprim (Bis-TMP), or any derivative or analog thereof promotes dimerization and activation of DHFR caspase-9 molecules. In some embodiments where constitutive expression of the suicide gene is initially desired, expression of the suicide gene may be turned off in the cell by contacting the cell with an inhibiting agent administered to the cell or to a mammal comprising the cell. The inhibiting agent selectively turns off expression. For example, caspase-9 is constitutively expressed in the cell and the addition of an inhibiting agent represses expression or activation of caspase-9. In one embodiment, the inhibiting agent is administered to the subject to repress expression of the suicide gene.

In some embodiments where constitutive expression of the suicide gene is initially desired, activation of the suicide gene product may be repressed in the cell by contacting the cell with an inhibiting agent, such as a solubilizing agent, administered to the cell or to a mammal comprising the cell. The inhibiting agent represses activation of the suicide gene product, such as by preventing dimerization of the caspase-9 molecules. In one embodiment, the solubilizing agent is administered to the subject to repress activation of the suicide gene product.

In some aspects, the suicide gene is not immunogenic to the cell comprising the suicide gene or host harboring the suicide gene. Although thymidine kinase (TK) may be employed, it can be immunogenic. Alternatively, examples of suicide genes that are not immunogenic to the host include caspase-9, caspase-8, and cytosine deaminase.

In yet another embodiment, suicide gene expression is linked in tandem to dimerization domains, which cause aggregation and degradation of the transcript, preventing cell-surface expression and hence function of the suicide gene.

In some embodiments, a solubilizing agent can be useful. Solubilization of the dimerization domains with a solubilizing agent, administered to the cell or to a mammal comprising the cell, prevents aggregation and allows the construct to egress through the secretory system.

Chimeric Antigen Receptor (CAR)

The field of T cell immunotherapy has evolved rapidly over the last several years, with groundbreaking success using chimeric antigen receptor (CAR) technology for cancer therapy. The basic principle behind CAR technology is that immunotyrosine-based activation motifs (ITAMs) contained in the cytoplasmic tail of the TCR CD3ζ chain can activate cytolytic T cells, independent of the rest of the TCR complex. Traditional TCR-based T cell activation depends on MHC-restricted peptide recognition plus co-stimulatory signals and is subject to tolerance mechanisms. CARs, in contrast, can be engineered to recognize any cell surface antigen with high affinity, and activation of the CAR is MHC-independent. Tumor specific CARs, having an extracellular antibody fused to CD137 and CD3ζ T cell cytoplasmic signaling domains, activate T cell cytotoxicity upon contact with antigen, causing CAR T cell expansion in vivo and production of memory CAR T cells, resulting in specific and permanent elimination of tumor cells.

As described herein, the present invention includes an engineered cell with a CAR and a suicide gene and a ligand comprising a radiolabeled tracer. The present invention encompasses a nucleic acid encoding a CAR or an engineered cell (e.g. T cell) comprising a CAR, wherein the CAR includes an antigen binding domain, a transmembrane domain and an intracellular domain.

One or more domains or a fragment of a domain of the CAR may be human. In one embodiment, the present invention includes a fully human CAR. The nucleic acid sequences coding for the desired domains can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than as a cloned molecule.

Example of CARs are described in U.S. Pat. Nos. 8,911,993, 8,906,682, 8,975,071, 8,916,381, 9,102,760, 9,101,584, and 9,102,761, all of which are incorporated herein by reference in their entireties.

Antigen Binding Domain

In one embodiment, the CAR comprises an antigen binding domain that binds to a B cell. Cell surface markers selectively found on B cells may act as an antigen that binds to the antigen binding domain of the CAR.

The anti-B cell antigen binding domain can include any domain that binds to the B cell and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof, such as a single chain variable fragment (scFv).

The antigen binding domain may bind one or more B cell antigens, such as, but not limited to, any surface marker selectively found on a B cell, such as a pro-B cell, pre-B cell, immature B cell, mature B cell, memory B cell, and plasma cell. In one embodiment, the antigen binding domain binds at least one B cell antigen, such as CD19, BCMA, and any combination thereof. In another embodiment, the antigen binding domain binds at least one B cell antigen, such as CD20, CD21, CD27, CD38, CD138, and any combination thereof.

In some instances, it is beneficial for the antigen binding domain to be derived from the same species in which the CAR will ultimately be used in. For example, for use in humans, it may be beneficial for the antigen binding domain of the CAR to comprise a human antibody, humanized antibody as described elsewhere herein, or a fragment thereof.

It is also beneficial that the antigen binding domain is operably linked to another domain of the CAR, such as the transmembrane domain or the intracellular domain, both described elsewhere herein, for expression in the cell. In one embodiment, a nucleic acid encoding the antigen binding domain is operably linked to a nucleic acid encoding a transmembrane domain and a nucleic acid encoding an intracellular domain.

In addition to B cell antigen binding domains, the antigen binding domain can be any antigen binding domain suitable for introduction into a CAR construct, where binding of the antigen binding domain to its cognate binding partner has a beneficial effect on a subject.

Transmembrane Domain

With respect to the transmembrane domain, the CAR can be designed to comprise a transmembrane domain that connects the antigen binding domain of the CAR to the intracellular domain. In one embodiment, the transmembrane domain is naturally associated with one or more of the domains in the CAR. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. In some instances, a variety of human hinges can be employed as well including the human Ig (immunoglobulin) hinge.

In one embodiment, the transmembrane domain may be synthetic, in which case it will comprise predominantly hydrophobic residues such as leucine and valine. Preferably a triplet of phenylalanine, tryptophan and valine will be found at each end of a synthetic transmembrane domain.

Intracellular Domain

The intracellular domain or otherwise the cytoplasmic domain of the CAR is responsible for activation of the cell in which the CAR is expressed. The term "intracellular domain" is thus meant to include any portion of the intracellular domain sufficient to transduce the activation signal. In one embodiment, the intracellular domain includes a domain responsible for an effector function. The term "effector function" refers to a specialized function of a cell. Effector function of a T cell, for example, may be cytolytic activity or helper activity including the secretion of cytokines.

In one embodiment, the intracellular domain of the CAR includes a domain responsible for signal activation and/or transduction. The intracellular domain may transmit signal activation via protein-protein interactions, biochemical changes or other response to alter the cell's metabolism, shape, gene expression, or other cellular response to activation of the chimeric intracellular signaling molecule.

Examples of an intracellular domain for use in the invention include, but are not limited to, the cytoplasmic portion of the T cell receptor (TCR) and any co-stimulatory molecule that acts in concert to initiate signal transduction following antigen receptor engagement, as well as any derivative or variant of these elements and any synthetic sequence that has the same functional capability. In one embodiment, the intracellular domain of the CAR comprises dual signaling domains. The dual signaling domains may include a fragment or domain from any of the molecules described herein.

Examples of the intracellular domain include a fragment or domain from one or more molecules or receptors including, but are not limited to, TCR, CD3 zeta, CD3 gamma, CD3 delta, CD3 epsilon, CD86, common FcR gamma, FcR beta (Fc Epsilon R1b), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In one embodiment, the intracellular domain of the CAR includes any portion of a co-stimulatory molecule, such as at least one signaling domain from CD3, CD27, CD28, CD83, CD86, CD127, 4-1BB, 4-1BBL, PD1, PD1L, T cell receptor (TCR), any derivative or variant thereof, any synthetic sequence thereof that has the same functional capability, and any combination thereof.

Between the antigen binding domain and the transmembrane domain of the CAR, or between the intracellular domain and the transmembrane domain of the CAR, a spacer domain may be incorporated. As used herein, the term "spacer domain" generally means any oligo- or polypeptide that functions to link the transmembrane domain to, either the antigen binding domain or, the intracellular domain in the polypeptide chain. In one embodiment, the spacer domain may comprise up to 300 amino acids, preferably 10 to 100 amino acids and most preferably 25 to 50 amino acids. In another embodiment, a short oligo- or polypeptide linker, preferably between 2 and 10 amino acids in length may form the linkage between the transmembrane domain and the intracellular domain of the CAR. An example of a linker includes a glycine-serine doublet.

In some embodiments, the CAR further comprises a signal peptide.

In some embodiments, the CAR further comprises a dimerization domain, such a dimerization domain from FKBP, F36V-FKBP, F36M-FKBP, E. coli dihydrofolate reductase (eDHFR) or similar molecule. In such an embodiment, the presence of CAR molecules on the surface of the modified T cell is prevented by spontaneous aggregation of the CAR molecules in the cytoplasm or other internal location in the cell.

CRISPR/Cas

The present invention further includes modifying the T cell described herein by deleting the endogenous T cell receptor (TCR) and/or major histocompatibility complex (MHC) molecules with genome editing technology to reduce or prevent the transmission of stimulatory signals through the endogenous TCR/MHC complex.

The CRISPR/Cas system is a facile and efficient system for inducing targeted genetic alterations. Target recognition by the Cas9 protein requires a 'seed' sequence within the guide RNA (gRNA) and a conserved di-nucleotide containing protospacer adjacent motif (PAM) sequence upstream of the gRNA-binding region. The CRISPR/CAS system can thereby be engineered to cleave virtually any DNA sequence by redesigning the gRNA in cell lines (such as 293T cells), primary cells, and CAR T cells. The CRISPR/CAS system can simultaneously target multiple genomic loci by co-expressing a single CAS9 protein with two or more gRNAs, making this system uniquely suited for multiple gene editing or synergistic activation of target genes.

One example of a CRISPR/Cas system used to inhibit gene expression, CRISPRi, is described in U.S. Publication No.: 2014/0068797. CRISPRi induces permanent gene disruption that utilizes the RNA-guided Cas9 endonuclease to introduce DNA double stranded breaks which trigger error-prone repair pathways to result in frame shift mutations. A catalytically dead Cas9 lacks endonuclease activity. When coexpressed with a guide RNA, a DNA recognition complex is generated that specifically interferes with transcriptional elongation, RNA polymerase binding, or transcription factor binding. This CRISPRi system efficiently represses expression of targeted genes.

CRISPR/Cas gene disruption occurs when a guide nucleic acid sequence specific for a target gene and a Cas endonuclease are introduced into a cell and form a complex that enables the Cas endonuclease to introduce a double strand break at the target gene. In one embodiment, the CRISPR system comprises an expression vector, such as, but not limited to, an pAd5F35-CRISPR vector. In one embodiment, the modified T cell described herein is further modified by introducing a Cas expression vector and a guide nucleic acid sequence specific for a gene into the modified T cell. In another embodiment, the Cas expression vector induces expression of Cas9 endonuclease. Other endonucleases may also be used, including but not limited to, T7, Cas3, Cas8a, Cas8b, Cas10d, Cse1, Csy1, Csn2, Cas4, Cas10, Csm2, Cmr5, Fok1, other nucleases known in the art, and any combination thereof.

The guide nucleic acid sequence is specific for a gene and targets that gene for Cas endonuclease-induced double strand breaks. The sequence of the guide nucleic acid sequence may be within a loci of the gene. In one embodiment, the guide nucleic acid sequence is at least 10, 11, 12, 13, 14, 15, 16, 17, 18, 19, 20, 21, 22, 23, 24, 25, 26, 27, 30, 31, 32, 33, 34, 35, 36, 37, 38, 39, 40 or more nucleotides in length.

The guide nucleic acid sequence may be specific for a T cell receptor (TCR) chain (such as an alpha, beta, gamma and/or delta chain), a major histocompatibility complex protein (such as a HLA class I molecule and/or HLA class II molecule), and any combination thereof.

The guide nucleic acid sequence includes a RNA sequence, a DNA sequence, a combination thereof (a RNA-DNA combination sequence), or a sequence with synthetic nucleotides. The guide nucleic acid sequence can be a single molecule or a double molecule. In one embodiment, the guide nucleic acid sequence comprises a single guide RNA.

In some embodiments, a T cell is modified to express a CAR and the CAR T cell is further modified to delete endogenous TCR or MHC molecules, such as before administration to a subject. In one embodiment, the CAR modified T cell described herein is further modified by deleting a gene selected from the group consisting of a T cell receptor (TCR) chain, a major histocompatibility complex protein, and any combination thereof. In another embodiment, the T cell is modified before administration to the subject in need thereof.

In some embodiments, a T cell is modified to express a CAR, administered to a subject, and then further modified in vivo to delete endogenous TCR or MHC molecules, such as through inducing targeted gene deletion. In one embodiment, the modified T cell described herein is modified by inducing a CRISPR/Cas system to minimize native reactivity of the modified T cell or host reactivity to the modified cell. In some embodiments, inducing the Cas expression vector comprises exposing the modified T cell to an agent that activates an inducible promoter in the Cas expression vector. In such an embodiment, the Cas expression vector includes an inducible promoter, such as one that is inducible by exposure to an antibiotic (e.g., by tetracycline or a derivative of tetracycline, for example doxycycline). However, it should be appreciated that other inducible promoters can be used. The inducing agent can be a selective condition (e.g., exposure to an agent, for example an antibiotic) that results in induction of the inducible promoter. This results in expression of the Cas expression vector.

In some embodiments, a T cell is modified to delete endogenous TCR or MHC molecules prior to modification to express the CAR. In some embodiments, the modified T cell is further modified by deleting TCR or MHC molecules prior to inducing expression of the suicide gene.

Introduction of Nucleic Acids

Methods of introducing nucleic acids into a cell include physical, biological and chemical methods. Physical methods for introducing a polynucleotide, such as RNA, into a host cell include calcium phosphate precipitation, lipofection, particle bombardment, microinjection, electroporation, and the like. RNA can be introduced into target cells using commercially available methods which include electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendorf, Hamburg Germany). RNA can also be introduced into cells using cationic liposome mediated transfection using lipofection, using polymer encapsulation, using peptide mediated transfection, or using biolistic particle delivery systems such as "gene guns" (see, for example, Nishikawa, et al. Hum Gene Ther., 12(8):861-70 (2001).

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Chol") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the nucleic acids in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Moreover, the nucleic acids may be introduced by any means, such as transducing the expanded T cells, transfecting the expanded T cells, and electroporating the expanded T cells. One nucleic acid may be introduced by one method and another nucleic acid may be introduced into the T cell by a different method.

RNA

In one embodiment, the nucleic acids introduced into the T cell are RNA. In another embodiment, the RNA is mRNA that comprises in vitro transcribed RNA or synthetic RNA. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is a chimeric membrane protein. By way of example, the template encodes an antibody, a fragment of an antibody or a portion of an antibody. By way of another example, the template comprises an extracellular domain comprising a single chain variable domain of an antibody, such as anti-CD3, and an intracellular domain of a co-stimulatory molecule. In one embodiment, the template for the RNA chimeric membrane protein encodes a chimeric membrane protein comprising an extracellular domain comprising an antigen binding domain derived from an antibody to a co-stimulatory molecule, and an intracellular domain derived from a portion of an intracellular domain of CD28 and 4-1BB.

PCR can be used to generate a template for in vitro transcription of mRNA which is then introduced into cells. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Chemical structures that have the ability to promote stability and/or translation efficiency of the RNA may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

In some embodiments, the RNA is electroporated into the cells, such as in vitro transcribed RNA.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the mRNAs with different structures and combination of their domains.

One advantage of RNA transfection methods of the invention is that RNA transfection is essentially transient and a vector-free. A RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. It is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct is delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Sources of T Cells

Prior to expansion, a source of T cells is obtained from a subject. Non-limiting examples of subjects include humans, dogs, cats, mice, rats, and transgenic species thereof. Preferably, the subject is a human. T cells can be obtained from a number of sources, including peripheral blood mononuclear cells, bone marrow, lymph node tissue, spleen tissue, umbilical cord, and tumors. In certain embodiments, any number of T cell lines available in the art, may be used. In certain embodiments, T cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, T cells are isolated from peripheral blood by lysing the red blood cells and depleting the monocytes, for example, by centrifugation through a PERCOLL™ gradient. Alternatively, T cells can be isolated from umbilical cord. In any event, a specific subpopulation of T cells can be further isolated by positive or negative selection techniques.

The cord blood mononuclear cells so isolated can be depleted of cells expressing certain antigens, including, but not limited to, CD34, CD8, CD14, CD19 and CD56. Depletion of these cells can be accomplished using an isolated antibody, a biological sample comprising an antibody, such as ascites, an antibody bound to a physical support, and a cell bound antibody.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In one embodiment, the population of T cells is comprised within cells such as peripheral blood mononuclear cells, cord blood cells, a purified population of T cells, and a T cell line. In another embodiment, peripheral blood mononuclear cells comprise the population of T cells. In yet another embodiment, purified T cells comprise the population of T cells.

Expansion of T Cells

As demonstrated by the data disclosed herein, expanding the T cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the T cells expand in the range of about 20 fold to about 50 fold.

Following culturing, the T cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The T cell medium may be replaced during the culture of the T cells at any time. Preferably, the T cell medium is replaced about every 2 to 3 days. The T cells are then harvested from the culture apparatus whereupon the T cells can be used immediately or cryopreserved to be stored for use at a later time. In one embodiment, the invention includes cryopreserving the expanded T cells. The cryopreserved T cells are thawed prior to introducing nucleic acids into the T cell.

In another embodiment, the method comprises isolating T cells and expanding the T cells. In another embodiment, the invention further comprises cryopreserving the T cells prior to expansion. In yet another embodiment, the cryopreserved T cells are thawed for electroporation with the RNA encoding the chimeric membrane protein.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore the number of population doublings of a culture is greater than the passage number. The expansion of cells (i.e., the number of population doublings) during the period between passaging depends on many factors, including but not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α. or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

The medium used to culture the T cells may include an agent that can co-stimulate the T cells. For example, an agent that can stimulate CD3 is an antibody to CD3, and an agent that can stimulate CD28 is an antibody to CD28. This is because, as demonstrated by the data disclosed herein, a cell isolated by the methods disclosed herein can be expanded approximately 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater. In one embodiment, the T cells expand in the range of about 20 fold to about 50 fold, or more by culturing the electroporated population.

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Methods of Treatment

The present invention includes methods for treating cancer, autoantibody or alloantibody diseases or conditions in a subject. In one embodiment, after tumor suppression or B cell depletion by the modified T cells, or following the onset of an adverse reaction to the engineered T cells, the engineered T cells are then selectively ablated in the subject by activating via a dimerization agent, a suicide gene that has been inserted into the engineered T cells.

In one aspect, the invention includes a method for assessing the efficacy or toxicity of an adoptive cell therapy. The modified engineered T cell comprises a nucleic acid encoding a chimeric antigen receptor, comprises a suicide gene and a radiolabeled tracer.

In one embodiment, the method further comprises inducing expression of the suicide gene to produce a suicide gene product that induces cell death of the modified T cell. In one such embodiment, administering an inducing agent induces expression of the suicide gene. In another embodiment, inducing expression of the suicide gene occurs after the modified T cell exerts cytotoxic function against B cells or after an onset of an adverse reaction in the subject to the modified T cell.

In one embodiment, the ligand binding domain is selected from the group consisting of FKBP, F36V-FKBP, and eDHFR.

In another embodiment, the ligand is a monomer or a dimer radiolabeled tracer. In some embodiments, the radiolabeled tracer is a monomer that does not activate the suicide gene.

In one embodiment, the radiolabeled tracer is selected from the group consisting of [$^{11}$C]-Shield-1; [$^{18}$F]-Shield-1; [$^{11}$C]-Trimethoprim ([$^{11}$C]-TMP) and [$^{18}$F]-Trimethoprim ([$^{18}$F]-TMP).

In another embodiment, the method further comprises activating a suicide gene product of the suicide gene to induce cell death of the modified T cell. In one such embodiment, administering an activating agent to promote dimerization of the suicide gene product to activate the suicide gene product. In another embodiment, activating the suicide gene product occurs after the modified T cell exerts cytotoxic function against B cells or after an onset of an adverse reaction in the subject to the modified T cell or after therapeutic effect is achieved.

In yet another embodiment, the method further comprises inhibiting expression of the suicide gene to inhibit cell death of the modified T cell. In one such embodiment, administering an inhibiting agent inhibits expression of the suicide gene. In another embodiment, administering the inhibiting agent occurs concurrently with administration of the modified T cell and continues as the modified T cell exerts cytotoxic function against B cells and may be ceased after an onset of an adverse reaction in the subject to the modified T cell.

The modified T cells can be administered to an animal, preferably a mammal, even more preferably a human, to suppress a tumor or an immune reaction, such as those common to an autoimmune disease or condition or an alloantibody disease or condition.

In addition, the modified T cells of the present invention can be used for the treatment of any condition in which a diminished or otherwise inhibited immune response, especially a cell-mediated immune response, is desired in order to treat or alleviate the disease.

Pharmaceutical Compositions

Pharmaceutical compositions of the present invention may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

In one aspect, the invention includes a pharmaceutical composition formulated for use in the method as described herein, the composition comprising an engineered cell comprising a nucleic acid encoding a suicide gene and a nucleic acid encoding a chimeric antigen receptor comprising an anti-B cell binding domain, a transmembrane domain, a costimulatory domain and an intracellular signaling domain and a ligand comprising a radiolabeled tracer. In some embodiments, the radiolabeled tracer is administered at very low concentrations, so its occupies 1-5% of the available target receptors. In some embodiments, the administered radiolabeled tracer does not have a measurable physiological effect on the subject.

The cells of the invention to be administered may be autologous, allogeneic or xenogeneic with respect to the subject undergoing therapy.

Cells of the invention can be administered in dosages and routes and at times to be determined in appropriate pre-clinical and clinical experimentation and trials. Cell compositions may be administered multiple times at dosages within these ranges. Administration of the cells of the invention may be combined with other methods useful to treat the desired disease or condition as determined by those of skill in the art.

The methods described herein may include administering the composition described herein via a combination therapy in prior to, concurrently with, or subsequent to another medication such as a chemotherapeutic. Accordingly, encompassed is a method of administration of chemotherapeutics, radiation, and/or immunotherapy in conjunction with the composition described herein. In one embodiment, the composition and chemotherapeutic, radiation, and/or immunotherapy are administered to the patient by one or more selected routes of administration sequentially. In another embodiment, a chemotherapeutic agent, radiation, and/or immunotherapy is administered before treatment with a composition described herein. In another embodiment, a chemotherapeutic agent, radiation, and/or immunotherapy is administered after treatment with the composition described herein. In still another embodiment, a chemotherapeutic agent, radiation, and/or immunotherapy is administered during treatment with a composition described herein.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the invention may be carried out in any convenient manner known to those of skill in the art. The cells of the present invention may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the invention are injected directly into a site of inflammation in the subject, a local disease site in the subject, a lymph node, an organ, a tumor, and the like.

In certain embodiments, the modified T cells are administered to a subject. Subsequent to administration, blood is drawn or apheresis is performed, and T cells are modified and expanded therefrom using the methods described here, and are then infused back into the patient. This process can be carried out multiple times every few weeks. In certain embodiments, T cells can be modified from blood draws of from 10 cc to 400 cc. In certain embodiments, T cells are modified from blood draws of 20 cc, 30cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

It should be understood that the method and compositions that would be useful in the present invention are not limited to the particular formulations set forth in the examples. The following examples are put forth so as to provide those of ordinary skill in the art with a complete disclosure and description of how to make and use the cells, expansion and culture methods, and therapeutic methods of the invention, and are not intended to limit the scope of what the inventors regard as their invention.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the invention, and, as such, may be considered in making and practicing the invention. Particularly useful techniques for particular embodiments will be discussed in the sections that follow.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The materials and methods employed in these experiments are now described.

Figure 4A:
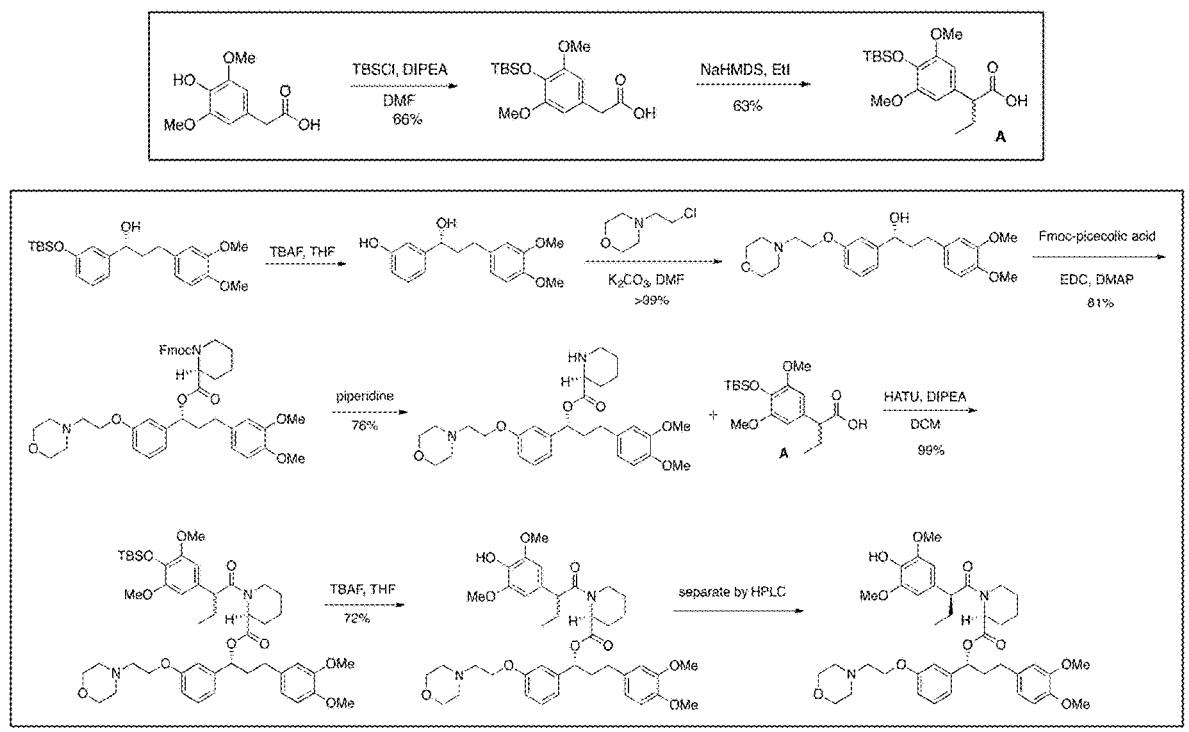
FIGS. 4A-4B are series of chemical structures illustrating the routes of synthesis of Shield-1 precursor.
Figure 4B:
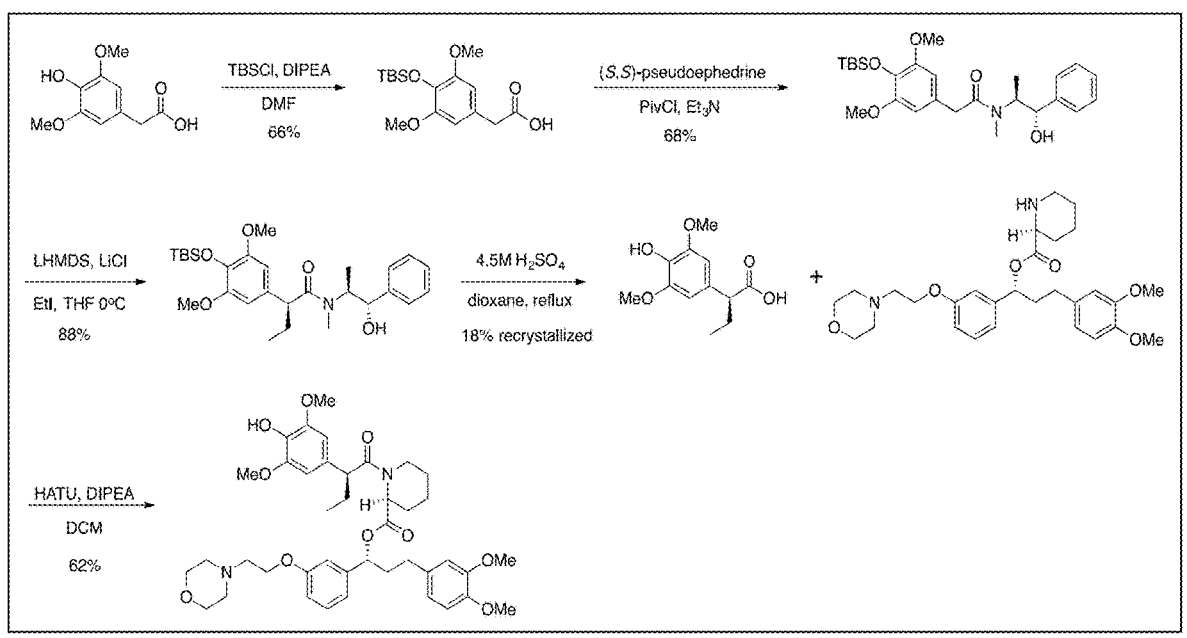

Shield-1 Precursor Synthesis (FIG. 4B):

To a solution of (S)-2-(4-hydroxy-3,5-dimethoxyphenyl) butanoic acid (79.2 mg, 0.15 mmol) in 1.5 mL dichloromethane was added N,N-diisopropylethylamine (107.7 µL, 0.61 mmol) and HATU (76.5 mg, 0.20 mmol). A solution of the amine ((R)-3-(3,4-dimethoxyphenyl)-1-(3-(2-morpholinoethoxy)phenyl)propyl (S)-piperidine-2-carboxylate) in dichloromethane was then added, and the reaction mixture was stirred at room temperature under nitrogen atmosphere for 24 h. The reaction was monitored by TLC and upon completion of reaction, the reaction mixture was quenched with saturated aqueous $NaHCO_3$ and extracted with dichloromethane (10 mL×3). The combined organic layers were dried over $Na_2SO_4$ and the solvent was evaporated under reduced pressure to obtain crude product. The crude material was purified by column chromatography on silica gel (5% methanol-dichloromethane) to obtained pure Shield-1 precursor. Yield 62% (69.8 mg); silica gel TLC $R_f$=0.33 (5% methanol-dichloromethane).

Figure 5A:
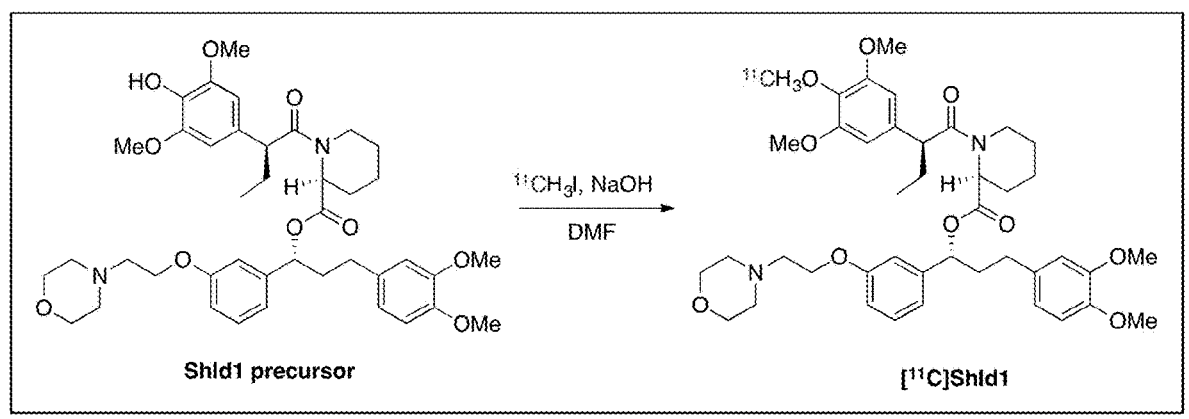
FIGS. 5A-5C are series of chemical structures and graphs depicting the properties of [$^{11}$C]Shld1.
Figure 5B:
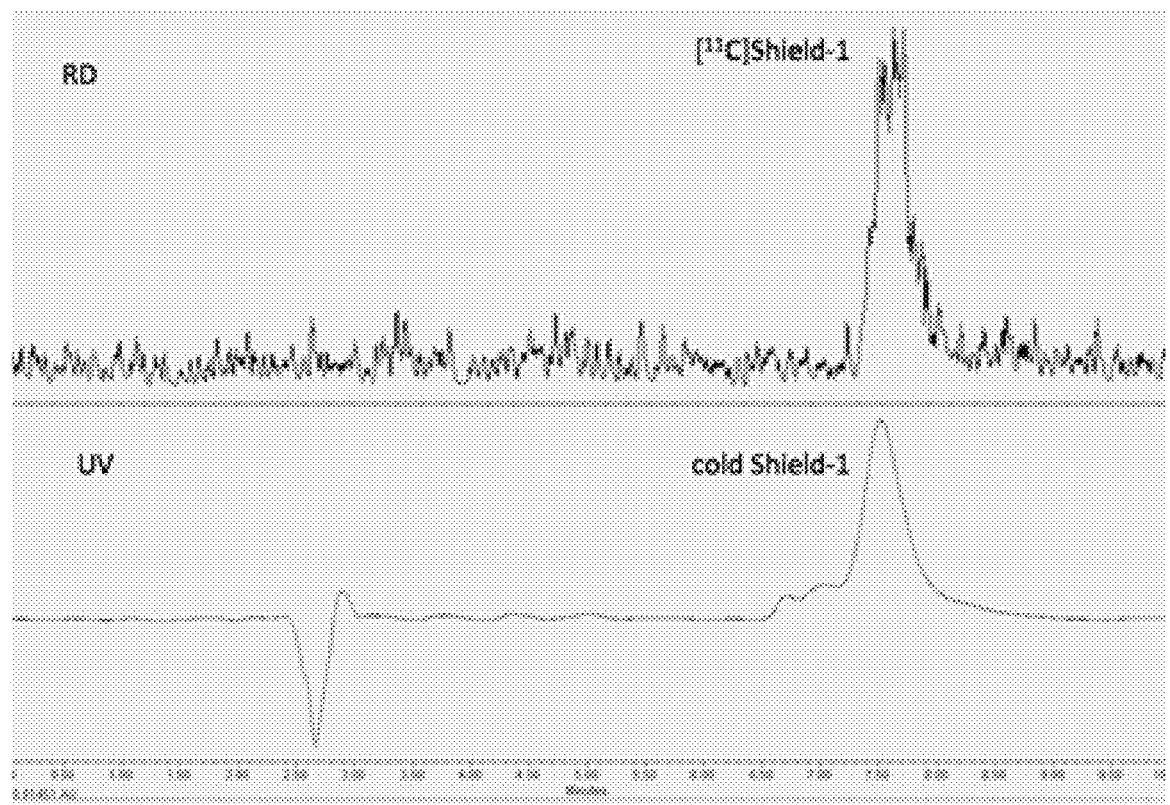

[$^{11}$C]Shield-1 Radiosynthesis (FIG. 5A):

The [$^{11}$C]$CO_2$ produced by the IBA Cyclone cyclotron is converted to [$^{11}$C]$CH_3I$ utilizing the GE PETtrace MeI Microlab system. Briefly, [$^{11}$C]$CO_2$ is transformed to [$^{11}$C]$CH_4$ using a nickel catalyst in the presence of hydrogen gas and the produced [$^{11}$C]$CH_4$ is then reacted with gaseous iodine at high temperature to form [$^{11}$C]$CH_3I$.

The radiochemical synthesis of [$^{11}$C]Shield1 was carried out by methylating the Shield-1 precursor. The produced [$^{11}$C]$CH_3I$ was bubbled to the reaction vial containing 1.0 mg Shield-1 precursor in 200 µL anhydrous DMF and 4 µL of 5N NaOH aqueous solution. The reaction mixture was then heated at 85° C. for 5 min, quenched with 1.5 mL of HPLC mobile phase and injected to a reversed-phase Phenomenex Luna C18 (250×10 mm) HPLC column for purification using 45:55 Acetonitrile/Water with 0.1% TFA as HPLC mobile phase at a flow rate of 5 mL/min. [$^{11}$C]Shield1 (Rt=15 min) was collected and diluted onto a vial containing 30 mL water, passed through a Sep-Pak C18 cartridge (Waters Corp.) and washed with 10 mL water. The product was then eluted with 1 mL of 200 proof ethanol followed by dilution with 9 mL phosphate buffered saline (PBS). The radiochemical yield is 5% with a radiochemical purity greater than 95% and a specific activity greater than 533 GBq/umoL.

[$^{11}$C]Shield-1 Cell Uptake Study (FIGS. 6A-6B)
Radioligand: [$^{11}$C]-Shield-1 in PBS
Cell line: HCT 116-F36V-FKBP and HCT116; HEK 293-F36V-FKBP and HEK293
Input cpm: ~240,000
Incubation media: Optimem (no FBS)+PBS (with $Ca^{2+}$ & $Mg^{2+}$) 1:1 (500 uL total volume)
Blocking agent: 10 uM FK506 in optimum
Plate 1×10$^7$ cells/well (6-well) 24 hours prior to uptake experiment
Trypsinize and divide cells in 2 eppendorf tube per well
Incubate with [$^{11}$C]-Shield-1 with or without blocking agent at 37° Celsius for 40 min (500 uL)
At end of incubation period, spin cells, wash 2× with 900 µL PBS
Protein assay-Lowry method were carried out to normalize results Western Blot Procedure:
Cell Lysis
Cells from T75 flask were harvested and lysed with 0.5 mL of lysis buffer (RIPA buffer+phosphatase inhibitor cocktail 2 & 3+protease inhibitor). Incubate on ice for 30 min, sonicate and spin at 12,00 rpm for 10 min.

Protein Determination by Lowry Method—Run Protein Gel
  Gel: TGX Miniprotean precast gels, 4-20% polyacrylamide gel, 10 well-50 uL, 8.6×6.7 cm (W×L) Cat #4561094
  Running buffer: 1× Tris/Glycine/SDS
  System: BioRad Tetra cell, 100 V, 1 hr 10 min
  Ladder: Biorad Precision plus Protein dual color standard
  Amount of protein loaded: 20 ug (1:1 with Laemmli solution)
  Transfer to PVDF membrane
  PVDF: Transblot Turbo Mini PVDF transfer pack (Cat #1704156)
  System: BioRad Transblot Turbo (Mixed MW, 7 min)
  Blocking: Odyssey blocking buffer in PBS (P/N 927-40000), 1 hr at room temp Aspirate media off dish and add 1 mL diluted ligand link label
  Incubate for 2 hrs
  Wash with PBS (2×)
  Add PBS with 10 mM glucose
  View fluorescence microscope (Zeiss)

FP-Shield-1 Synthesis (FIG. 21):
  To a solution of Shield-1 precursor (5.0 mg, 6.8 nmols) in DMF (0.2 mL) was added 12 N NaOH (54) and 1-bromo-3-fluoropropane (3.79 mg, 27.2 nmols). The reaction mixture heated to 80° C. for 15 mins, and monitored by LC-MS. Upon completion of reaction, the crude material was purified by HPLC using reverse phase C-18 silica gel column (40% acetonitrile-water in 0.1% trifluoroacetic acid) to obtain pure FP-Shield-1. Yield 28% (1.5 mg).

Synthesis of the TMP Library (FIG. 25)

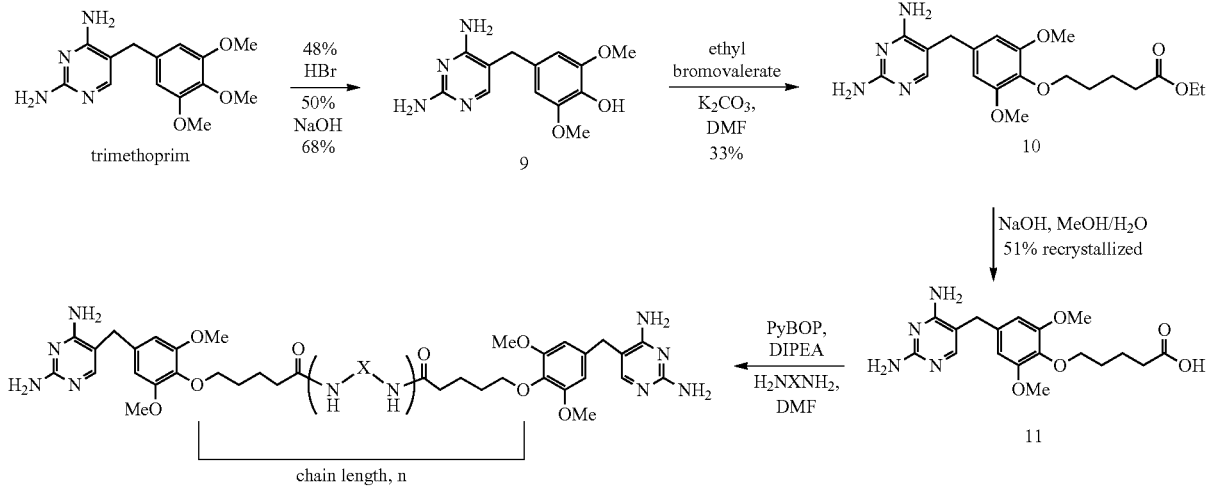

Scheme 1. Synthesis of Bis-TMP-16, -21, -27, and -33.

Wash in TBST (1×TBS buffer+0.1% Tween 20)
Incubate in primary Antibody: Anti-HA (12CA5), 0.4 mg/mL in PBS, dilution used 1:1,000 mouse monoclonal: Anti-GapDH, 0.2 mg/mL, dilution used 1:1,000; goat polyclonal in TBST with 5% blocking buffer, overnight at 4° C. with gentle shaking
Wash 4× with TBST, 10 min each with gentle shaking
Incubate in secondary antibody: Goat anti-mouse IgG, dilution used 1:10,000, 800 CW-Licor: Donkey anti-goat IgG, dilution used 1:10,000, 680 RD-Licor in TBST with 5% blocking buffer, 1 hr at room temp with gentle shaking
Wash 4× with TBST, 10 min each with gentle shaking
Read Odyssey CLx Imaging system Li-COR Biosciences
Labeling of DHFR-icasp9 Cells with Ligandlink (Fluorescein Label with TMP)
  Day 1 plate cells on glass bottom dish 35 mm

| HCT116 DHFR-icasp9 | $1.5 \times 10^6$ |
| HEK293 | $1.5 \times 10^6$ |
| MB231-luc | $2.0 \times 10^6$ |

Day 2 labeling of cells with ligand link
  Add 30 uL DMF:acetic acid to 1 vial ligand link (1 mM)
  Dilute to 2 uM in DMEM with 10% FBS Ethyl 5-(4-((2,4-diaminopyrimidin-5-yl)methyl)-2,6-dimethoxyphenoxy)pentanoate (10): DMSO (16 mL) was added to a degassed flask containing phenol 9 (2.20 g, 7.97 mmols, 1 equiv). The resulting solution was evacuated then purged 3 times with nitrogen gas. DBU (1.31 mL, 8.76 mmol, 1.1 equiv) and ethyl-1-5-bromovalerate (1.39 mL, 8.76 mmol, 1.1 equiv) were added sequentially and the final mixture was evacuated then purged 3 time with nitrogen gas. After 2 h, the mixture was partially concentrated via rotavap and the resulting concentrated solution was loaded onto a silica gel column and eluted with 2-10% methanol in dichloromethane to provide 1.27 g (39% yield) of a white solid. HRMS calcd: 405.2138, obsvd: 405.2138

5-(4-((2,4-diaminopyrimidin-5-yl)methyl)-2,6-dimethoxyphenoxy)pentanoic acid (11): To a solution of ester 10 (652 mg, 1.61 mmol, 1 equiv) in methanol (16 mL, 0.1 M) was added aqueous sodium hydroxide solution (1 M, 4.8 mL, 4.8 mmol, 3 equiv). After 2.5 h, methanol was removed via rotary evaporation and the resulting aqueous solution was neutralized to pH7 using an aqueous hydrochloric acid solution (1 M, ca. 4.5 mL) which resulted in precipitation of a white solid. The solids were washed with cold water then dried to provide the desired acid (308.6 mg, 51% yield). HRMS: calcd: 377.1825, obser: 377.1833

N,N'-(Ethane-1,2-diyl)bis(5-(4-((2,4-diaminopyrimidin-5-yl)methyl)-2,6-dimethoxyphenoxy)pentanamide) (Bis-TMP-16): Acid 11 (42.7 mg, 0.113 mmols, 2.5 equiv) and benzotriazol-1-yl-oxytripyrrolidinophosphonium hexafluorophosphate (PyBOP, 94.4 mg, 0.18 mmol, 4 equiv) were combined and evacuated then purged with nitrogen gas. DMF (1 mL) and DIPEA (47 μL, 0.27 mmol, 6 equiv) added and allowed to stir for 1.5 h. 1,2-Diaminoethane (3 μL, 0.045 mmol, 1 equiv) was added and the resulting solution was allowed to stir overnight. The crude sample was purified by prep-HPLC to afford the desired product Bis-TMP-16 (22.5 mg, 16% yield) as a clear oil. HRMS: calcd: 7774048, observ: 777.4028

N,N'-(oxybis(propane-3,1-diyl))bis(5-(4-((2,4-diaminopyrimidin-5-yl)methyl)-2,6-dimethoxyphenoxy)pentanamide) (Bis-TMP-21): Acid 11 (59.0 mg, 0.1157 mmols, 2.5 equiv) and benzotriazol-1-yl-oxytripyrrolidinophosphonium hexafluorophosphate (PyBOP, 130.5 mg, 0.251 mmol, 4 equiv) were combined and evacuated then purged with nitrogen gas. DMF (1 mL) and D1PEA (66 μl, 0.376 mmol, 6 equiv) were added and allowed to stir for 30 min. Bis(3-aminopropyl) ether (8.3 mg, 0.063 mmol, 1 equiv) was added and the resulting solution was allowed to stir overnight. The crude sample was purified by prep-HPLC to afford the desired product Bis-TMP-21 (55.7 mg, 41% yield) as a clear oil. HRMS: calcd: 849.4614, observ: 849.4623

N,N'-(((oxybis(ethane-2,1-diyl))bis(oxy))bis(propane-3,1-diyl))bis(5-(4-((2,4-diaminopyrimidin-5-yl)methyl)-2,6-dimethoxyphenoxy)pentanamide) (Bis-TMP-27): Acid 11 (41.9 mg, 0.11 mmols, 2.5 equiv) and benzotriazol-1-yl-oxytripyrrolidinophosphonium hexafluorophosphate (PyBOP, 93 mg, 0.178 mmol, 4 equiv) were combined and evacuated then purged with nitrogen gas. DMF (1 mL) and DIPEA (46 μL, 0.267 mmol, 6 equiv) were added and allowed to stir for 30 min. 4,7,10-Trioxa-1,13-tridecanediamine (9.8 μL, 0.045 mmol, 1 equiv) was added and the resulting solution was allowed to stir overnight. The crude sample was purified by prep-HPLC to afford the desired product Bis-TMP-27 (18.8 mg, 30% yield) as a clear oil. HRMS [M+Na]: calcd: 959.4967, observ: 959.4959

N,N'-(4,7,10,13,16-pentaoxanonadecane-1,19-diyl)bis(5-(4-((2,4-diaminopyrimidin-5-yl)methyl)-2,6-dimethoxyphenoxy)pentanamide) (Bis-TMP-33): Acid 11 (60.3 mg, 0.16 mmols, 2.5 equiv) and benzotriazol-1-yl-oxytripyrrolidinophosphonium hexafluorophosphate (PyBOP, 133 mg, 0.26 mmol, 4 equiv) were combined and evacuated then purged with nitrogen gas, DMF (1 mL) and DIPEA (67 μL, 0.384 mmol, 6 equiv) were added and allowed to stir for 30 min. 1,19-Diamino-4,7,10,13,16-pentaoxanonadecane (19.8 mg, 0.064 mmol, 1 equiv) was added and the resulting solution was allowed to stir overnight. The crude sample was purified by prep-HPLC to afford the desired product Bis-TMP-33.

Scheme 2. Synthesis of Bis-TMP-6, -8, -10

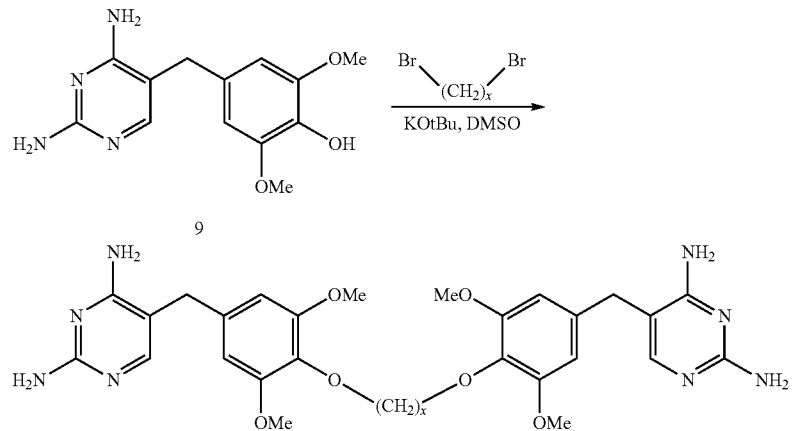

5,5'-(((butane-1,4-diylbis(oxy))bis(3,5-dimethoxy-4,1-phenylene))bis(methylene))bis(pyrimidine-2,4-diamine) (Bis-TMP-6): DMSO (5.0 mL) was added to a degassed flask containing phenol 9 (200 mg, 0.724 mmols, 1.0 equiv). The resulting solution was evacuated then purged 3 times with nitrogen gas. Potassium tert-butoxide (97.5 mg, 0.87 mmol, 1.2 equiv) and 1,4-dibromobutane (28.2 μL, 0.23 mmol, 0.33 equiv) were added sequentially and the final mixture was evacuated then purged 3 time with nitrogen gas. The solution was stirred at room temperature (rt) for 48 h, and the mixture was partially concentrated under reduced pressure and the resulting concentrated liquid was purified by column chromatography on reverse phase C-18 silica gel (acetonitrile-water) to obtain Bis-TMP-6. Yield 21% (93.1 mg).

5,5'-(((hexane-1,6-diylbis(oxy))bis(3,5-dimethoxy-4,1-phenylene))bis(methylene))bis(pyrimidine-2,4-diamine) (Bis-TMP-S): DMSO (5.0 mL) was added to a degassed flask containing phenol 9 (500 mg, 1.81 mmols, 1 equiv).

The resulting solution was evacuated then purged 3 times with nitrogen gas. Potassium tert-butoxide (243 mg, 2.17 mmol, 1.2 equiv) and 1,6-dibromohexane (90 μL, 0.59 mmol, 0.33 equiv) were added sequentially and the final mixture was evacuated then purged 3 time with nitrogen gas. The solution was stirred at room temperature (rt) for 48 h, and the mixture was partially concentrated under reduced pressure and the resulting concentrated liquid was purified by column chromatography on reverse phase C-18 silica gel (acetonitrile-water) to obtain Bis-TMP-8. Yield 19% (220 mg).

5,5'-(((octane-1,8-diylbis(oxy))bis(3,5-dimethoxy-4,1-phenylene))bis(methylene))bis(pyrimidine-2,4-diamine) (Bis-TMP-10): DMSO (2.0 mL) was added to a degassed flask containing phenol 9 (200 mg, 0.72 mmols, 1 equiv). The resulting solution was evacuated then purged 3 times with nitrogen gas. Potassium tert-butoxide (97 mg, 0.86 mmol, 1.2 equiv) and 1,8-dibromooctane (44 μL, 0.23 mmol, 0.33 equiv) were added sequentially and the final mixture was evacuated then purged 3 time with nitrogen gas. The solution was stirred at rt for 48 h, and the mixture was partially concentrated under reduced pressure and the resulting concentrated liquid was purified by column chromatography on reverse phase C-18 silica gel (acetonitrile-water) to obtain Bis-TMP-10. Yield 17% (84.2 mg).

Scheme 3. Synthesis of Tris-TMP-7

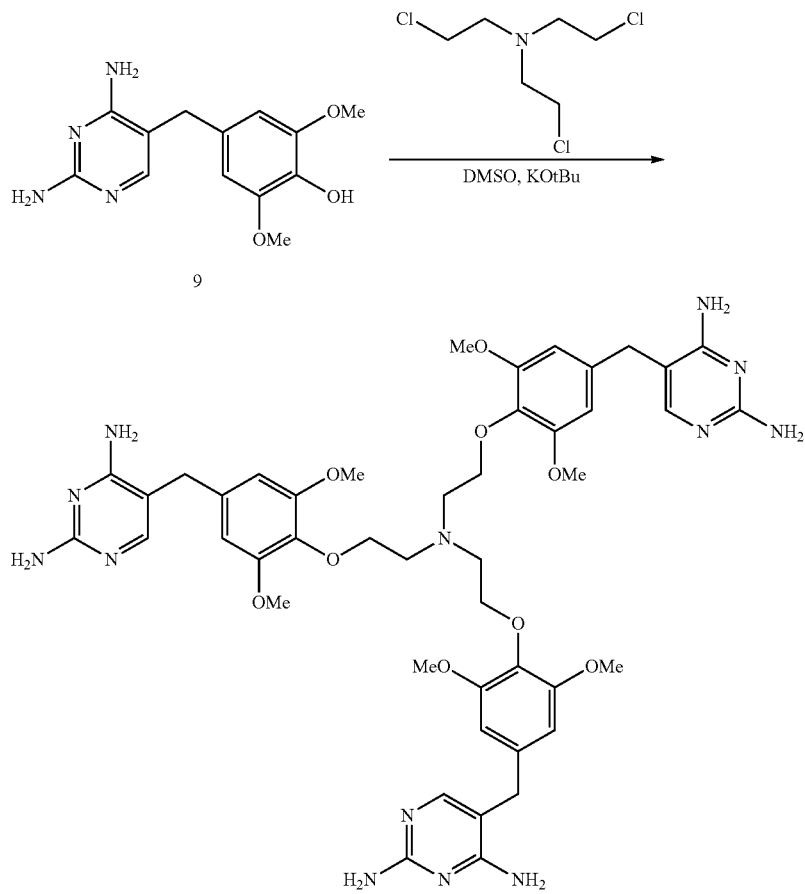

5-(4-(2-(bis(2-(4-((2,4-diaminopyrimidin-5-yl)methyl)-2,6-dimethoxyphenoxy)ethyl)amino)ethoxy)-3,5-dimethoxybenzyl)pyrimidine-2,4-diamine (Tris-TMP-7): DMSO (2.0 mL) was added to a degassed flask containing phenol 9 (229 mg, 0.82 mmols, 1 equiv). The resulting solution was evacuated then purged 3 times with nitrogen gas. Potassium tert-butoxide (112 mg, 0.93 mmol, 4.0 equiv) and tris(2-chloroethyl)amine (50 μL, 0.21 mmol, 0.25 equiv) were added sequentially and the final mixture was evacuated then purged 3 times with nitrogen gas. The solution was stirred at rt for 48 h, and the mixture was partially concentrated under reduced pressure and the resulting concentrated liquid was purified by column chromatography on reverse phase C-18 silica gel (acetonitrile-water) to obtain Tris-TMP-7. Yield 7% (48.1 mg).

Procedure for DHFR-iCasp9 Cell Kill Assay with Bis-TMP Compounds:

Cell Culture
  Cell lines (MDA-MB231-luc transduced with DHFR-icasp9 with different linker lengths) were cultured in DMEM (Gibco) with 10% fetal bovine serum (Sigma), 100 U/mL penicillin and 100 ug/mL streptomycin (Invitrogen).
  Incubation is done at 37° C. with 5% CO2

Cell Assay
  Cells were plated on 96 well black plate, 3×10⁴ cells/well.
  The next day, cells were treated with varying concentrations of Bis-TMP compounds (Bis-TMP-#).
  Cells were incubated for 24 hours and luciferin was added (120 ug/mL), after which bioluminescence was measured using Perkin Elmer Enspire Multi-mode Plate reader.

Luminescence Assay with HCT116-L106P-tsLuc Cells Following Treatment with Shield-1 Compounds:
  Day 1: Plate 50,000 cells/50 uL/well on 96 well black plate.
  Day 2:
    Add compounds (FP-Shield-1, control Shield-1 in 50 uL volume).
    Incubate for 24 h at 37° C. with $CO_2$.
  Day 3: Add luciferin and read immediately.

The results of the experiments are now described.

Example 1

Novel PET Radiotracers for Imaging CAR T Cells with a Dual Function Report Gene

A dual function reporter gene that serves as both an imaging agent and a potent suicide gene could find widespread application as a safety switch in cell-based therapies, which would open the door to numerous imaging applications. Since CAR T cell therapy and other gene therapies carry significant risk, which includes cytokine release syndrome, neurological toxicity, on-target/off-tumor toxicity, insertional oncogenesis, graft versus host disease, and off-target antigen recognition, the elegance of a dual function suicide-reporter is key from both a regulatory and patient perspective.

This invention contemplate the use of the mutant human FK506 binding protein, F36V-FKBP, as a dual function reporter gene, since it has a number of high affinity ligands such as Shield-1 that could serve as novel PET radiotracers, and it has been successfully utilized in humans as a component of the iCasp9 suicide gene (Di Stasi et al., N Engl J Med. 2011; 365(18):1673-1683). The iCasp9 system is based on human caspase 9, in which the recruitment domain of the caspase has been replaced by F36V-FKBP. This allows the caspase pathway to be activated by the small molecule AP1903, which is a dimer of Shield-1 that causes apoptosis via dimerization of the F36V-FKBP/caspase 9 fusion protein (FIG. 1A). iCasp9 has been used as a safety switch in patients that underwent stem-cell transplantation for relapsed acute leukemia, and a single dose of AP1903 was given to several patients who developed graft-versus-host disease (GVHD); more than 90% of the modified T cells were eliminated within 30 min after administration of AP1903, and the GVHD was terminated without abrogating immune reconstitution (Di Stasi et al., N Engl J Med. 2011; 365(18):1673-1683; Zhou et al., Blood. 2014;123(25):3895-3905). Of note, the iCasp9 system has not been found to be immunogenic. Currently, the iCasp9 system is being utilized in several phase 1/2 clinical trials as a suicide gene for stem cell transplantation, as well as anti-GD2 CAR T cell therapy for neuroblastoma/sarcoma.

Figure 1B:
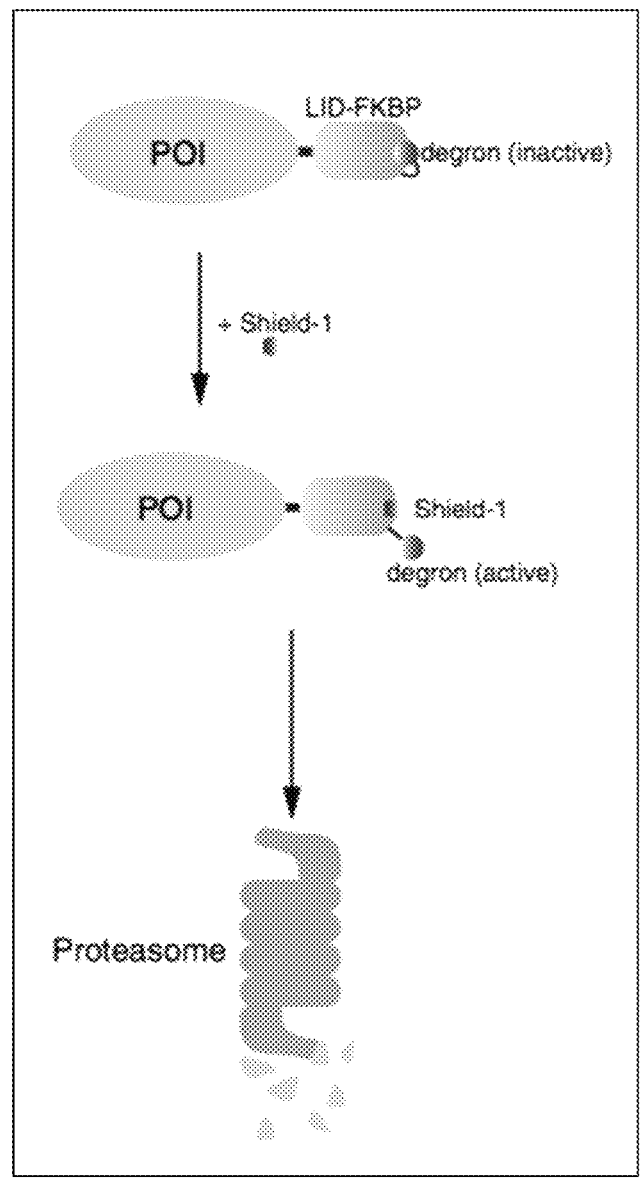

F36V-FKBP has also been used in the ligand-induced degradation (LID) system, in which protein expression can be controlled by the addition of Shield-1 (FIG. 1B) (Bonger et al., Nat Chem Biol. 2011; 7(8):531-537). The LID system is based on the addition of a degradation sequence (degron) to the C terminus of F36V-FKBP, which is then fused to a protein of interest. In the absence of Shield-1 the degron is bound to FKBP and the protein is stable. However, when Shield-1 is present, it binds tightly to FKBP, displaces the degron, and induces rapid degradation of the LID domain and the fused protein of interest. Although the LID system has not yet been tested in humans, it should be non-immunogenic given its similarity to the iCasp9 system. In preclinical studies the LID system can be used to control expression of the CAR in T cells in a dose-dependent manner using Shield-1, with an $IC_{50}$ in the nM range.

Figure 2:
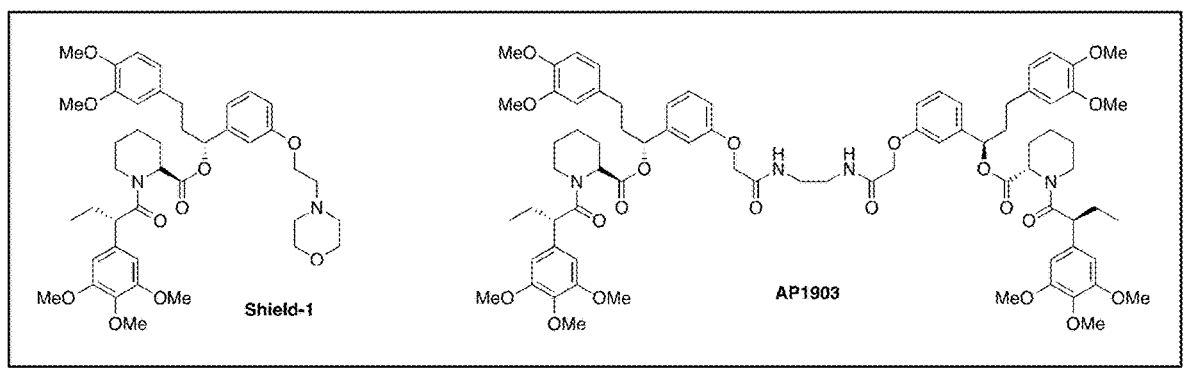
FIG. 2 is a graph depicting the chemical structures of Shield-1 and AP1903.

[$^{11}$C] or [$^{18}$F] radiolabeled Shield-1 (Shld1) can serve as a novel PET radiotracer for imaging F36V-FKBP because it has a high affinity for the mutant protein with an $IC_{50}$ of 3.3 nM, it is specific for the mutant protein versus wild-type FKBP, and it is a monomeric version of AP1903 which has already been given to humans without any reported serious adverse events (FIG. 2). Ligands such as Shield-1 and AP1903 that possess a "bump" in the FKBP binding domain have been shown to bind more tightly to the mutant F36V-FKBP relative to the wild-type protein by greater than three orders of magnitude; thus binding of [$^{11}$C/$^{18}$F]Shld1 to wild-type FKBP should be negligible (Clackson et al., Proc Natl Acad Sci USA. 1998; 95(18):10437-10442). Additionally, [$^{11}$C/$^{18}$F]Shld1 has no effect on the CART cells, since the radiotracer is a monomer and only the dimer (AP1903) is capable of activating the caspase pathway.

Figure 3A:
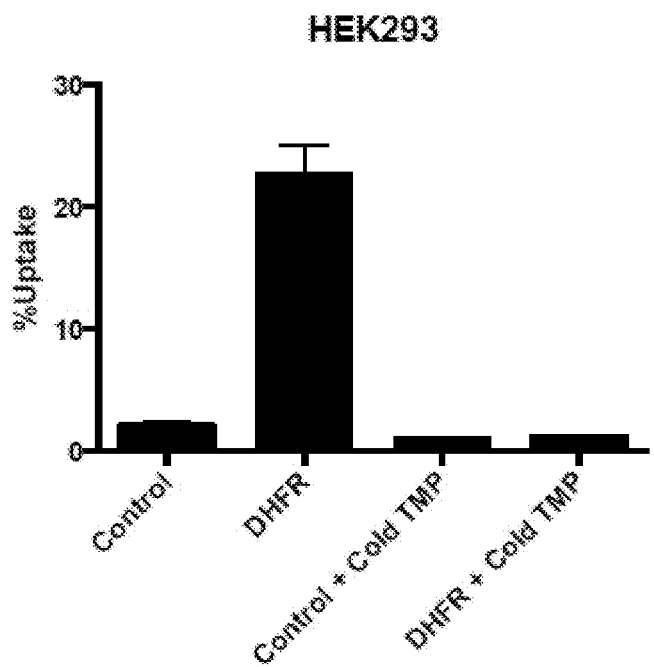
FIGS. 3A-3B are series of graphs and images showing cell uptake with [$^{11}$C]TMP.
Figure 3B:
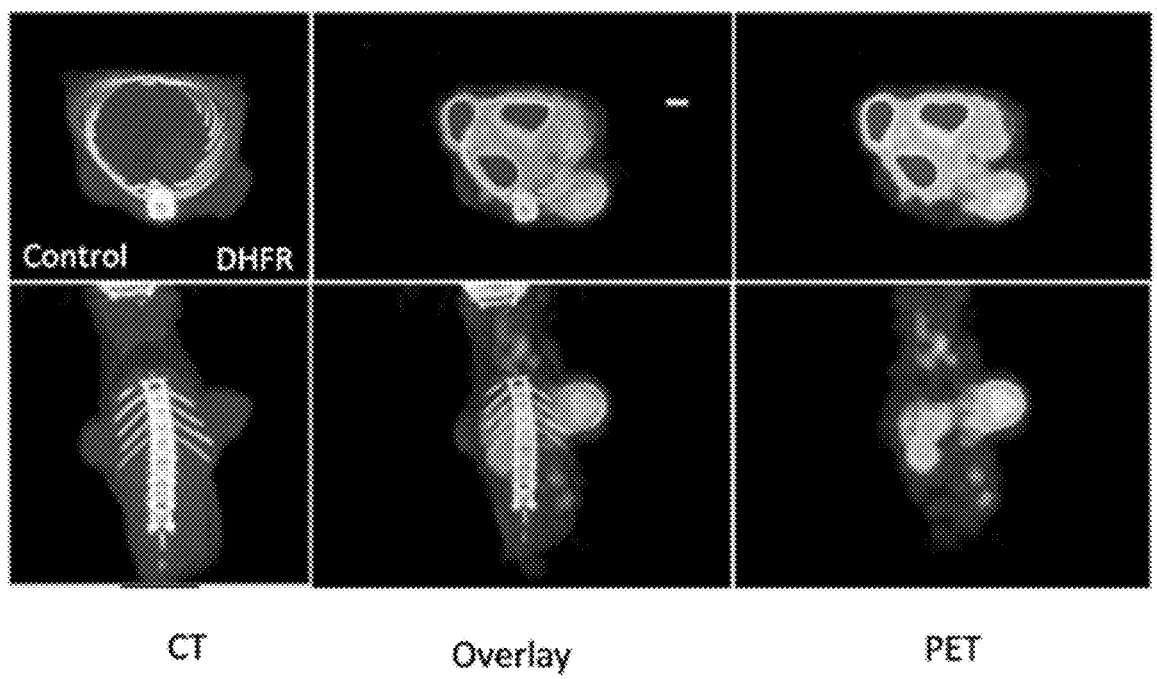

This invention also includes the use of a modified iCasp9 dual function suicide-reporter gene in which the ligand binding domain (F36V-FKBP) has been replaced by E. coli dihydrofolate reductase (eDHFR). [$^{11}$C] labeled trimethoprim (TMP) was previously synthesized as a novel PET radiotracer with high affinity for the DHFR enzyme. The novel PET radiotracer, [$^{11}$C]TMP, was synthesized by methylation with [$^{11}$C]methyl iodide; the desired product was isolated with high specific activity (500-1000 mCi/mmol) and 50-60% radiochemical yield. Cell uptake studies were then performed with HEK293 cells that had been transduced with the DHFR reporter gene, with untransduced HEK293 cells as a control; 10 uM cold TMP was also used as a control, to confirm that the uptake of [$^{11}$C]TMP was blocked in the presence of a large excess of cold TMP. The results are shown in FIG. 3A, in which the transduced HEK293 cells demonstrated 23% uptake of [$^{11}$C]TMP, versus less than 1-2% uptake in the controls. For the animal imaging experiments, DHFR positive and DHFR negative HCT116 tumors were xenografted subcutaneously (10 million cells) to the shoulders of nude mice. The tumors were grown for 10 days and imaged using small animal PET followed by CT imaging. A representative animal is shown at imaging time point 85-90 min after ~1 mCi of [$^{11}$C]TMP injected IV through the tail vein (FIG. 3B). As can be seen in the images, the DHFR positive tumors demonstrated markedly increased radiotracer uptake relative to the control tumor (Sellmyer et al., Proc. Natl. Acad. Sci. U.S.A. 114: 8372-8377 (2017). Sellmyer et al., Mol Ther 25: 120-126 (2017).

The eDHFR/[$^{11}$C/$^{18}$F]TMP system was shown to be highly sensitive for detecting transduced cells via PET imaging, and has only mild physiologic radiotracer uptake within the liver and GI tract. Since TMP is able to cross the blood-brain barrier (BBB), and is an established ligand for inducing protein dimerization, it has the potential to be an excellent PET radiotracer for a dual function suicide-reporter gene. Thus the eDHFR iCasp9 system is capable of being imaged with [$^{18}$F]TMP.

This invention includes a novel dual function suicide-reporter gene that is capable of being imaged with a PET radiotracer and is also capable of serving as a potent suicide gene. This invention utilizes (1) the iCasp9 suicide gene that is currently in clinical use (based on F36V-FKBP/Shld1), and (2) the modified iCasp9 system based on eDHFR/TMP.

Example 2

Synthesis and In Vitro Studies with [$^{11}$C]Shld1

Figure 5C:
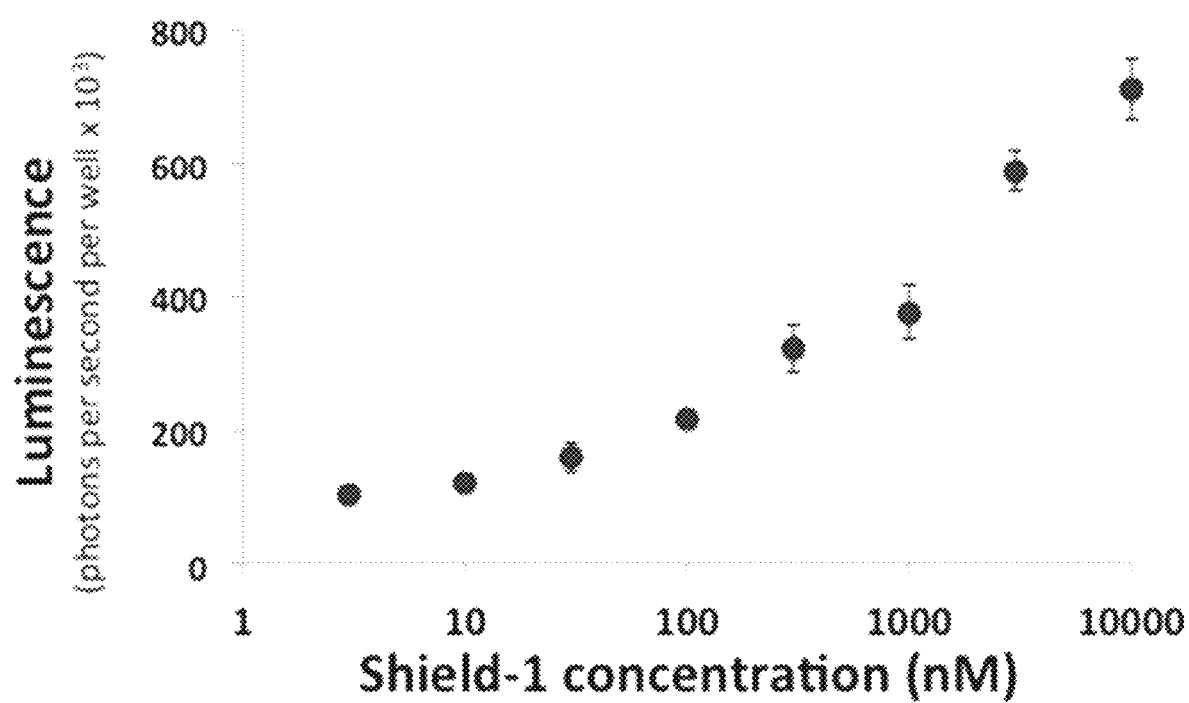

[$^{11}$C]Shld1 was successfully synthesized, and demonstrated that the novel radiotracer is equivalent to commercially available cold Shld1 (FIGS. 4A-4B, 5A-5B). The Shld1 precursor was synthesized via a modified multi-step route (Amara et al., Proc Natl Acad Sci USA. 1997; 94(20): 10618-10623; Yang et al., J Med Chem. 2000; 43(6):1135-1142). Methylation of the precursor with [$^{11}$C]methyl iodide yielded [$^{11}$C]Shld1 in 5% radiochemical yield (FIG. 5A) with a specific activity of >533 GBq/μmoL at end of bombardment. Analysis of the radiotracer by HPLC (FIG. 5B) demonstrated co-elution of [$^{11}$C]Shld1 at the same time as the reference standard; radiochemical purity is >95%. The functionality of the synthesized Shld1 was evaluated using HCT116 cells expressing luciferase fused to the FKBP12 L106P destabilizing domain (L106P-tsLuc). HCT116 cells treated with varying concentrations of synthesized Shld1 induced equivalent protein stabilization when compared to the literature (FIG. 5C) (Banaszynski et al., Nat Med. 2008; 14(10):1123-1127).

Figure 6A:
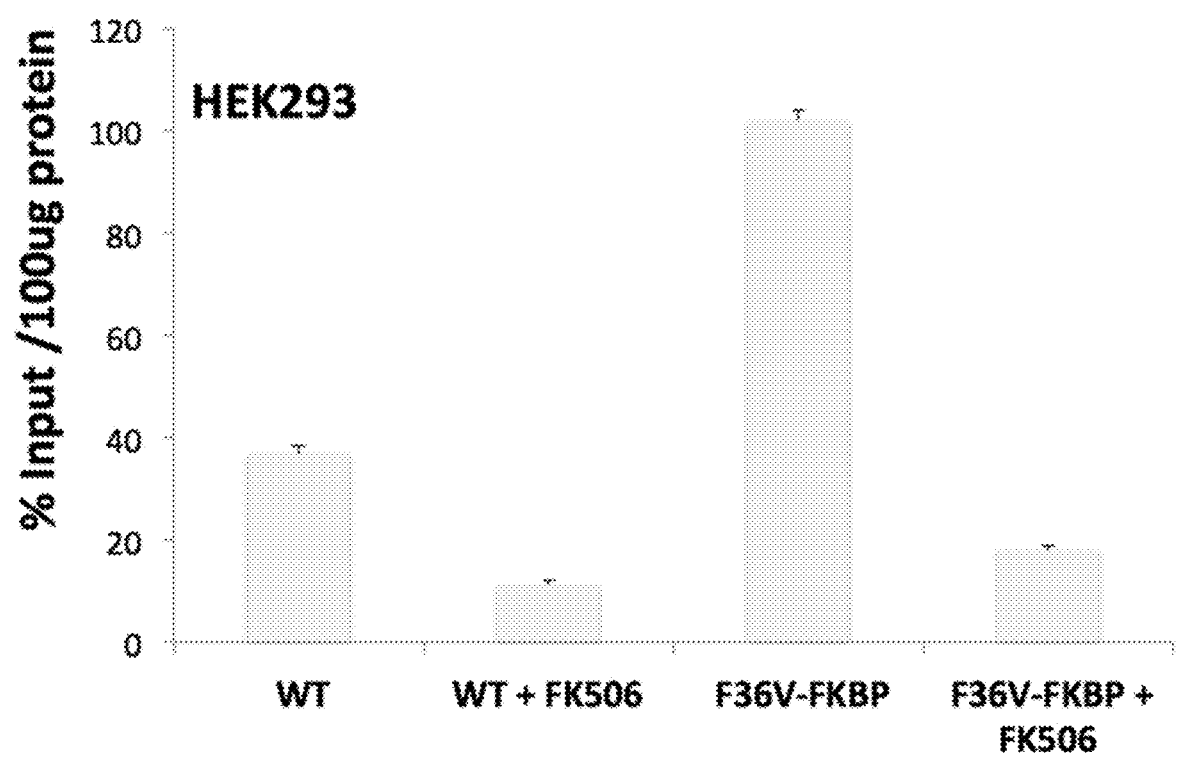
FIGS. 6A-6B are series of histograms showing [$^{11}$C]Shld1 uptake in HEK293 cells (FIG. 6A) and in HCT116 cells (FIG. 6B) after 40 min. HEK293 and HCT116 cells transduced with F36V-FKBP take up C-11 Shield-1 well at 40 minutes. The uptake can be blocked by a large excess of cold FK506 (10 μM), and WT cells do not take up C-11 Shield-1, thus the amount of nonspecific binding is low.
Figure 6B:
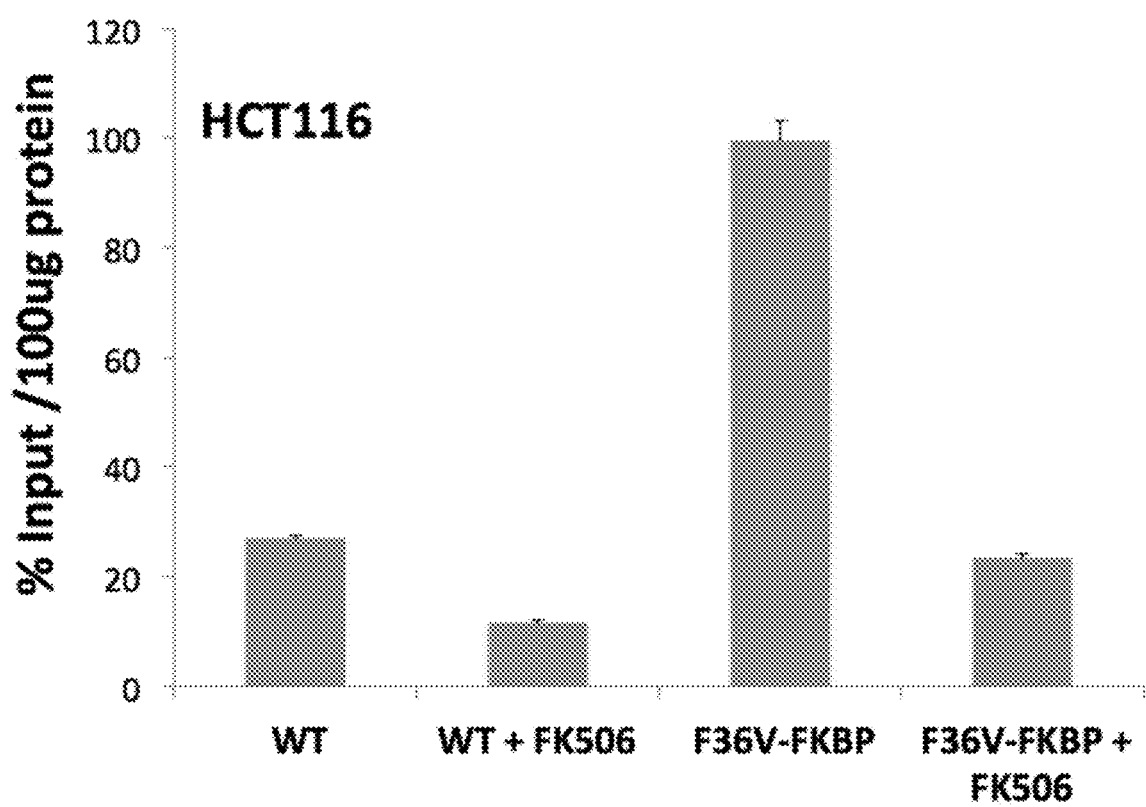
Figure 7:
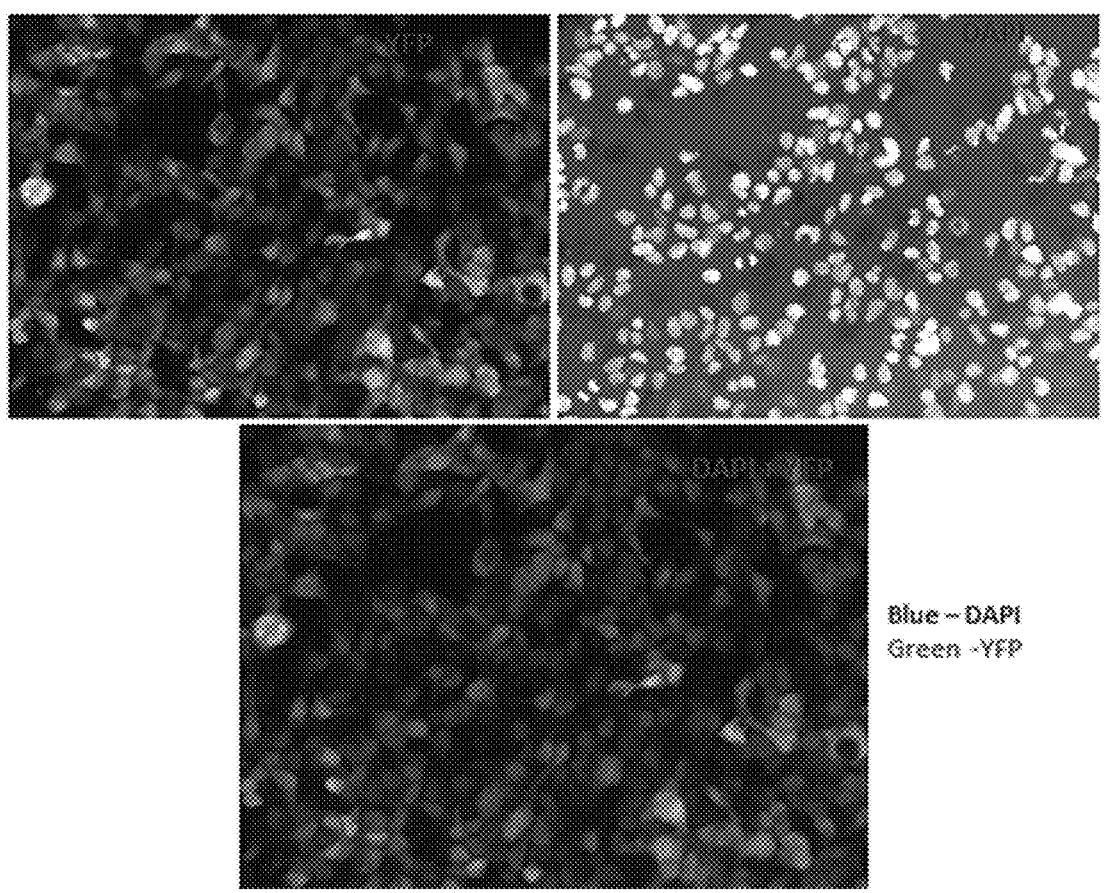
FIG. 7 is a series of images illustrating HEK 293-F36V-FKBP-YFP cells. The nucleus was stained with DAPI.

Cell uptake studies with [$^{11}$C]Shld-1 were performed with HEK293 and HCT116 cells that were transduced with the F36V-FKBP reporter gene (via a retroviral vector), with untransduced HEK293 and HCT116 cells as a control; FK506 (10 μM) was used as a blocking agent. Transduced HEK293 and HCT116 cells both demonstrated [$^{11}$C]Shld-1 uptake close to 100% input/100 μg protein, at 40 min, with substantially less uptake in the untransduced cells and the blocking experiment (FIGS. 6A-6B).

Figure 9:
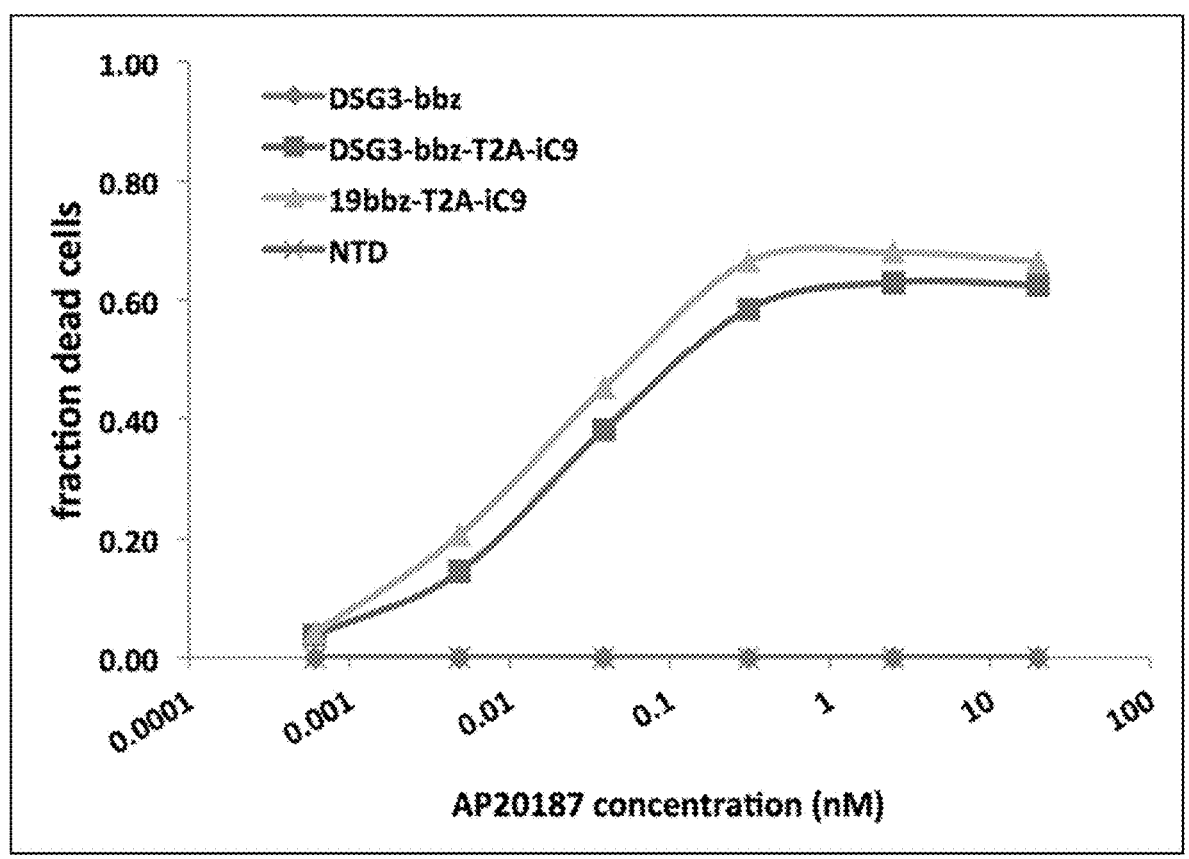
FIG. 9 is a graph demonstrating caspase activation following treatment of CAR T cells with AP20187. The inducible caspase 9 was incorporated into CART cells directed against desmoglein-3, and was activated by treatment with varying concentrations of AP20187, a chemical inducer of dimerization which is an analog of AP1903.

The iCasp9 system has been previously incorporated into CAR T cells directed against desmoglein-3 by others for studying pemphigus. T cells were transduced with two different CARs containing iCasp9 (iC9) and one CAR without iC9. The inducible caspase 9 was activated by treatment with varying concentrations of AP20187, a chemical inducer of dimerization which is an analog of AP1903 (FIG. 9). Of note is that the fraction of dead cells is less than 100% because not all of the cells were transduced. The $IC_{50}$ of AP20187 is <0.1 nM. Nontransduced cells (NTD) and cells without iC9 were not killed by AP20187.

Example 3

Biodistribution of [$^{11}$C]Shld1 in Mice

Biodistribution studies were performed to determine the major organs of [$^{11}$C]Shld1 uptake, measure the rate of radiotracer clearance from the blood pool, and assess the ability of [$^{11}$C]Shld1 to cross the BBB.

Figure 8:
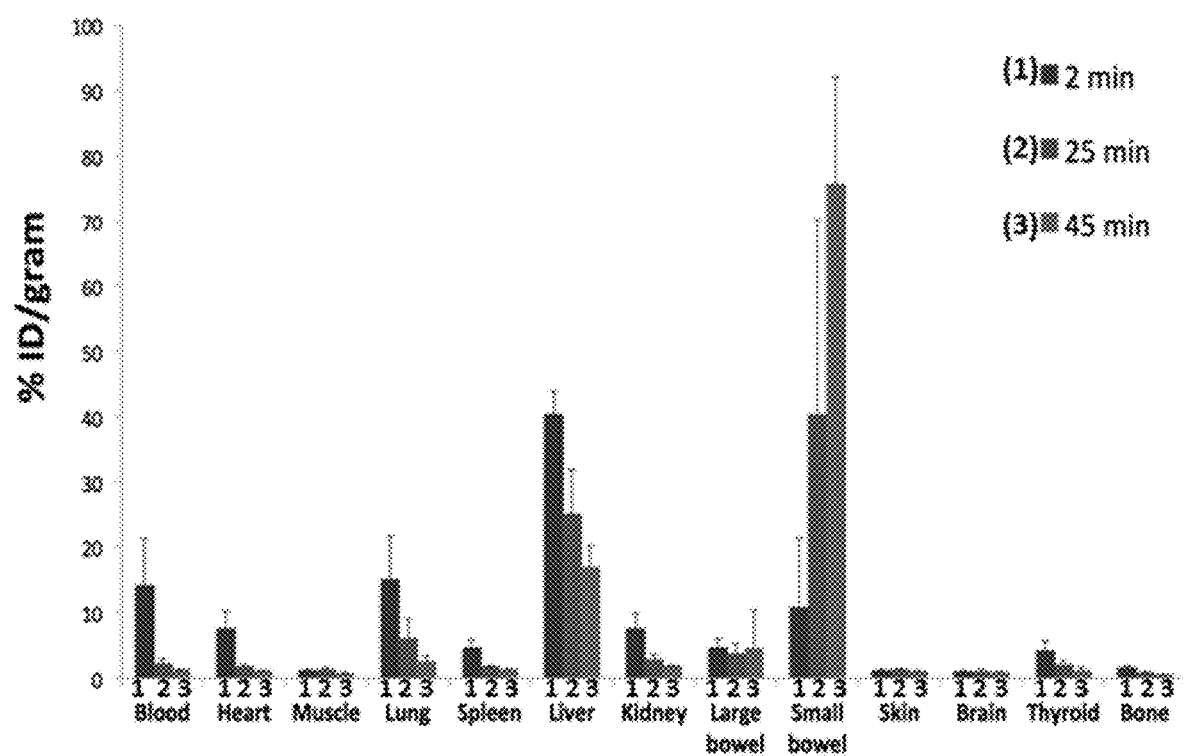
FIG. 8 is a histogram depicting [$^{11}$C]Shield-1 biodistribution study. 50 μCi of [$^{11}$C]-Shield-1 was injected via the tail vein, and mice were sacrificed at 2 min, 25 min, and 45 min following injection of radiotracer (n=4 mice per time point).

Biodistribution data for [$^{11}$C]Shld1 were collected at 2 min, 25 min, and 45 min following injection of radiotracer via the tail vein (50 µCi), with 4 mice (C57BL/6) per time point (FIG. 8). Organs were harvested and counted using a well gamma counter. Standard deviations were calculated for each sample.

Example 4

Synthesis of FP Shield-1 and Comparison of Its Affinity with Shield-1

Figure 10A:
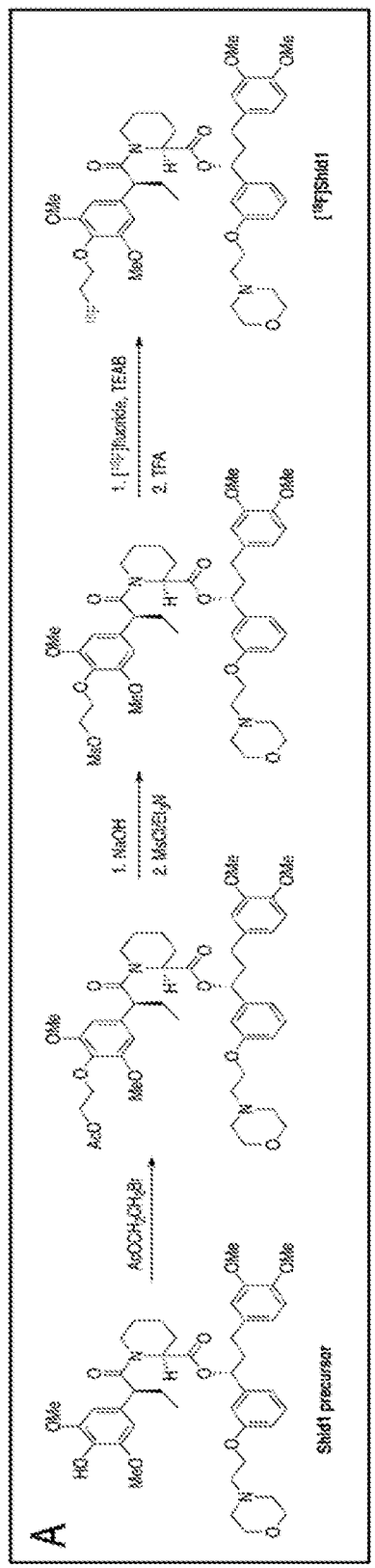
FIGS. 10A-10B is a series of chemical structures illustrating the synthesis of [$^{18}$F]-fluoroethyl-Shield-1 (FIG. 10A) and other [$^{18}$F] labeled derivatives of Shield-1 (FIG. 10B).
Figure 10B:
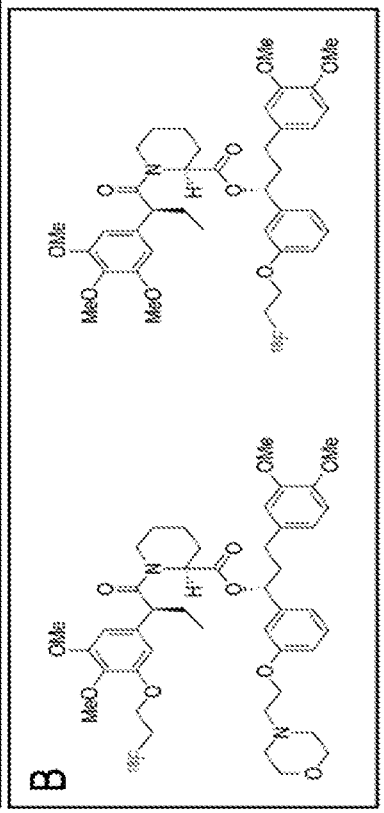
Figure 21:
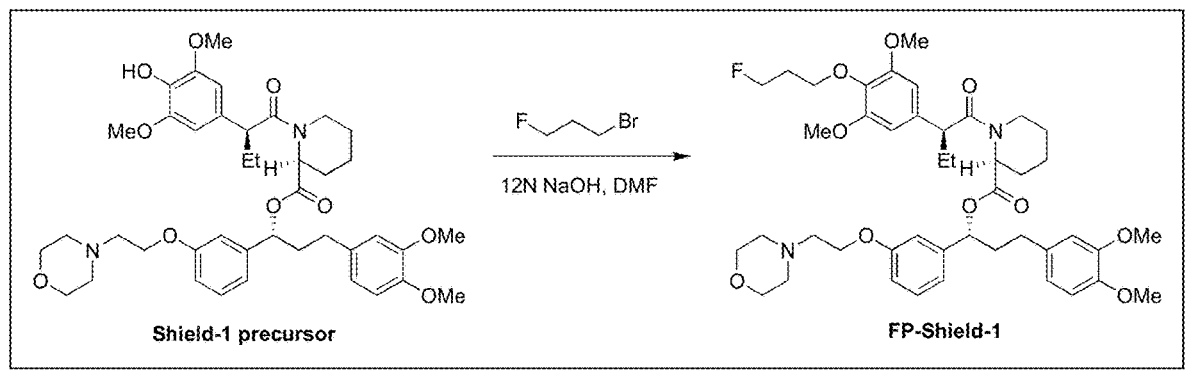
FIG. 21 is a series of chemical structures illustrating the synthesis of fluoropropyl-Shield-1 (FP-Shield-1) from the Shield-1 precursor.
Figure 22:
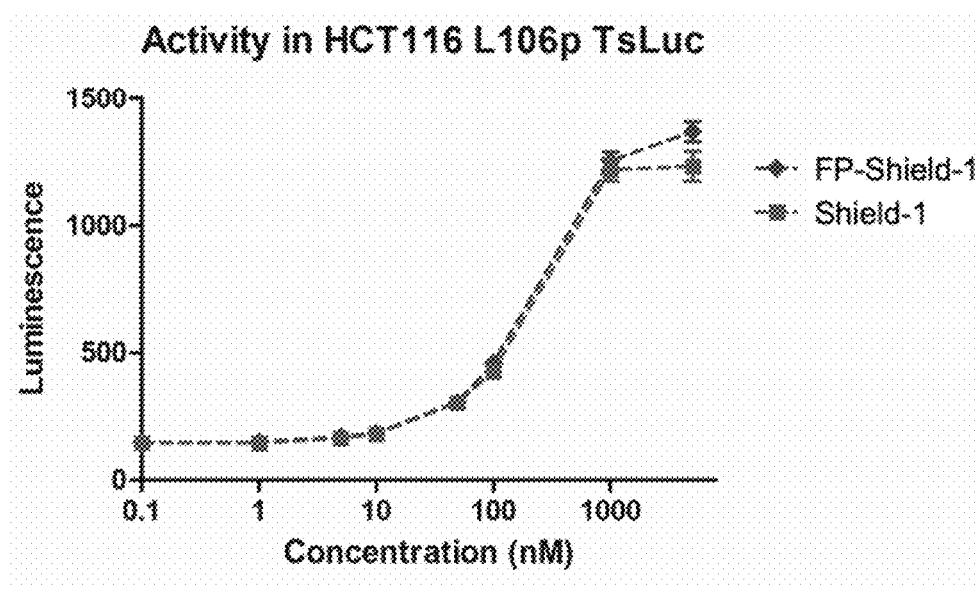
FIG. 22 is a graph depicting the luminescence of HCT116 cells stably expressing L106P-tsLuc following treatment with increasing concentrations of either cold Shield-1 (from Cheminpharma, LLC) or FP-Shield-1, and incubation with luciferin. This graph demonstrates that the affinity of FP-Shield-1 for F36V-FKBP is similar to commercially available Shield-1.
Figure 23A:
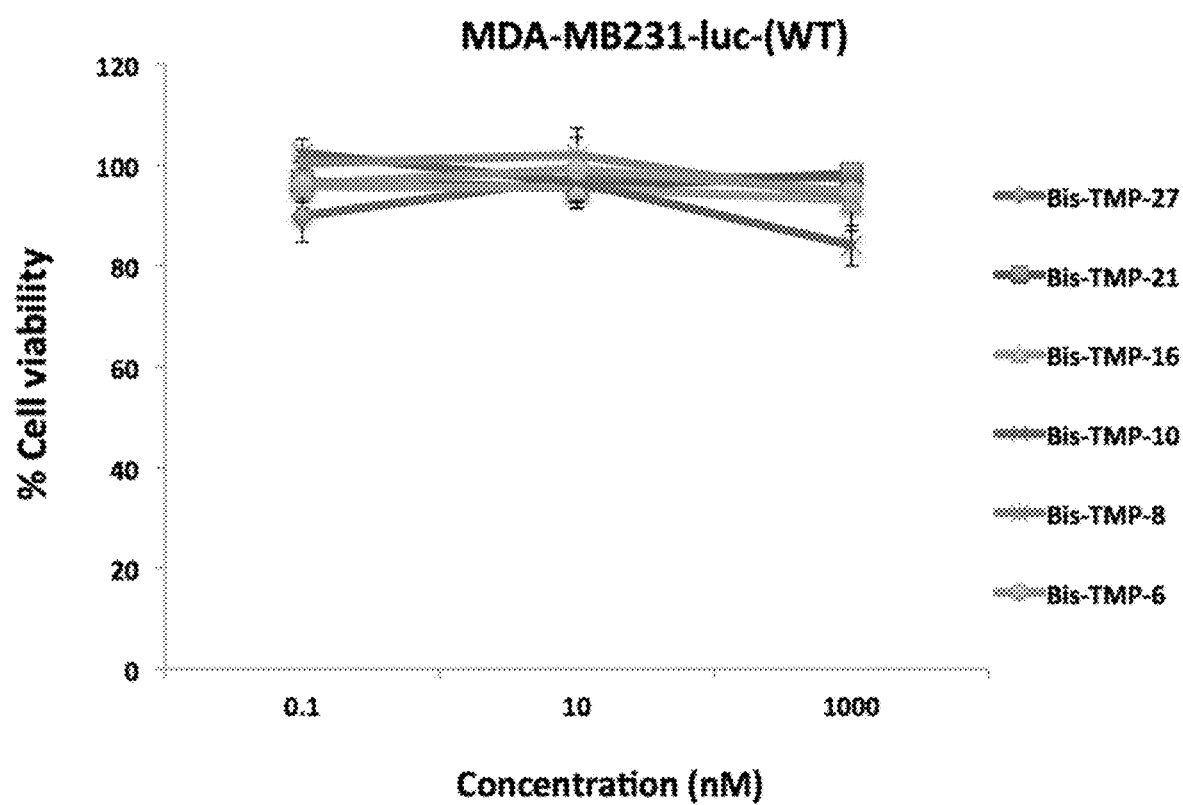
FIGS. 23A-23F are a series of graphs depicting the % viability of MDA-MB231 cells that have been transduced with different DHFR-iCasp9 constructs, and treated with a variety of Bis-TMP compounds at increasing concentrations. The linker between DHFR and iCasp9 was modified to be 5, 6, 9, 15, or 18 amino acids in length. The linker between the TMP molecules in the Bis-TMP compounds was modified to be 6, 8, 10, 16, 21, or 27 atoms in length. Wild-type MDA-MB231 cells were also evaluated as a control. Most combinations did not produce any cell killing; only DHFR-iCasp9 linkers of 15 or 18 amino acids, and Bis-TMP linkers of 21 and 27 atoms demonstrated cell killing.
Figure 23B:
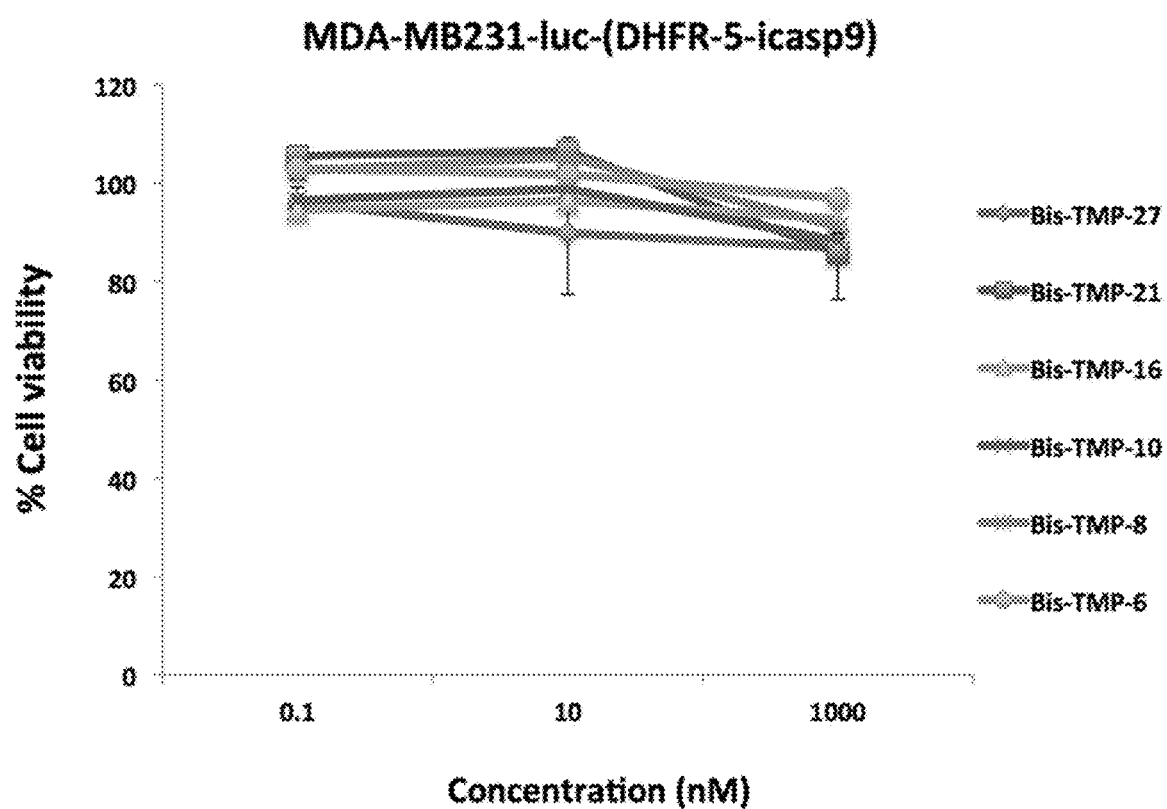
Figure 23C:
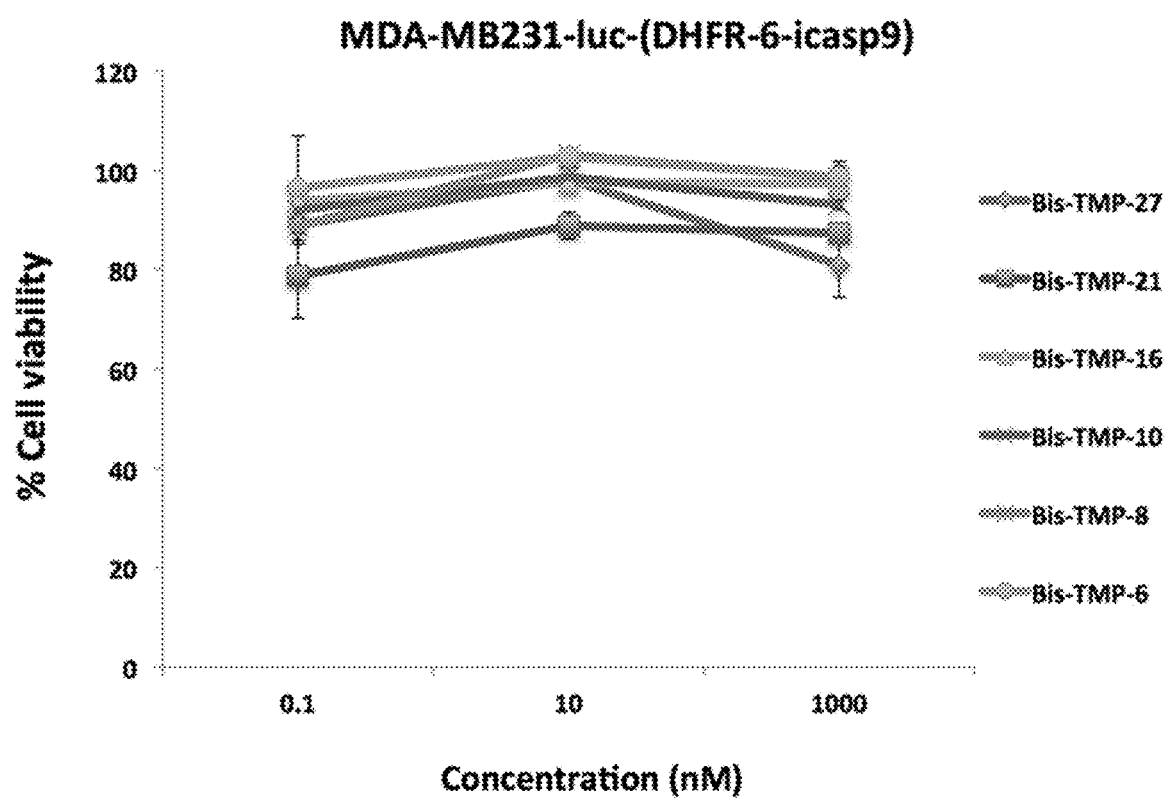
Figure 23D:
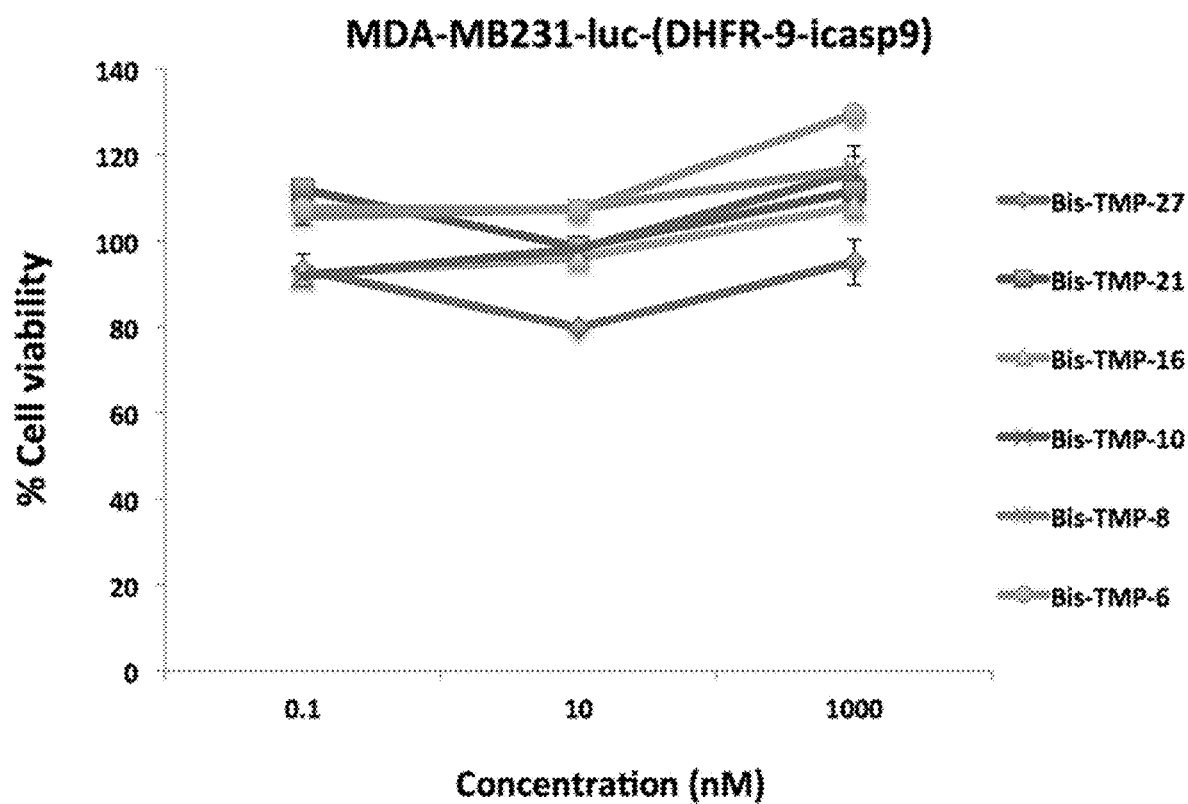
Figure 23E:
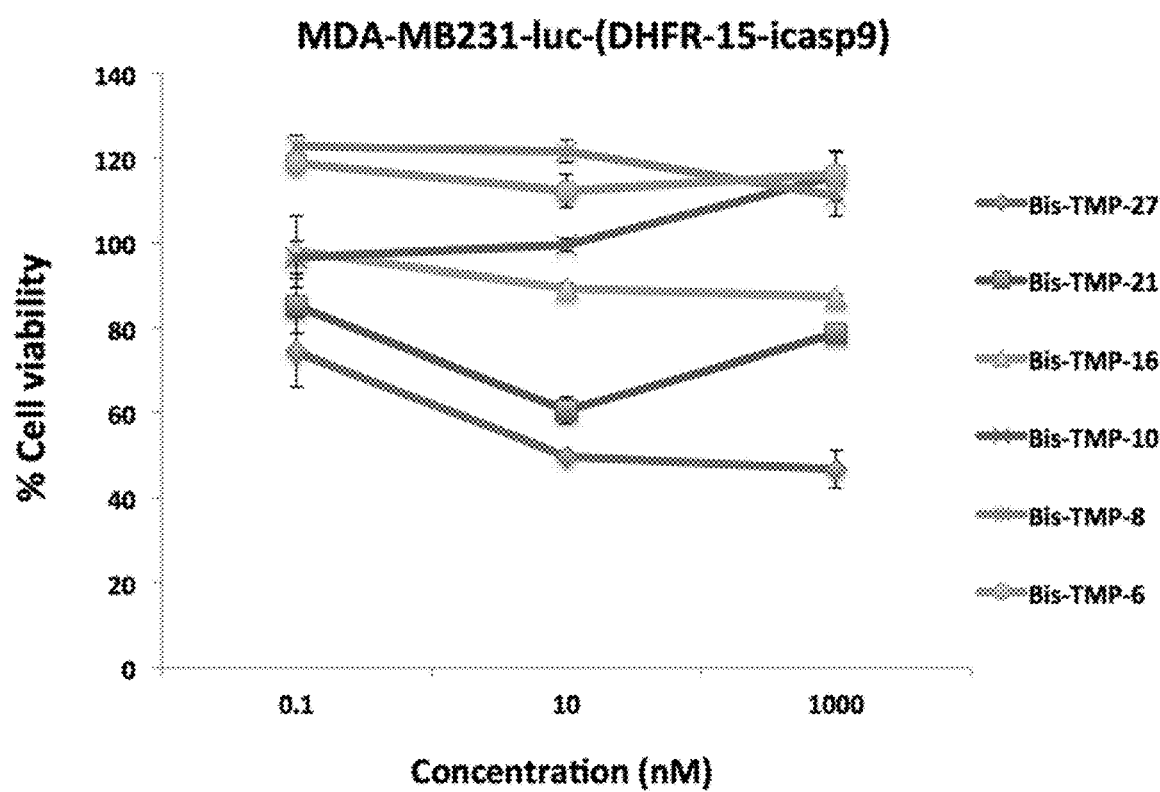
Figure 23F:
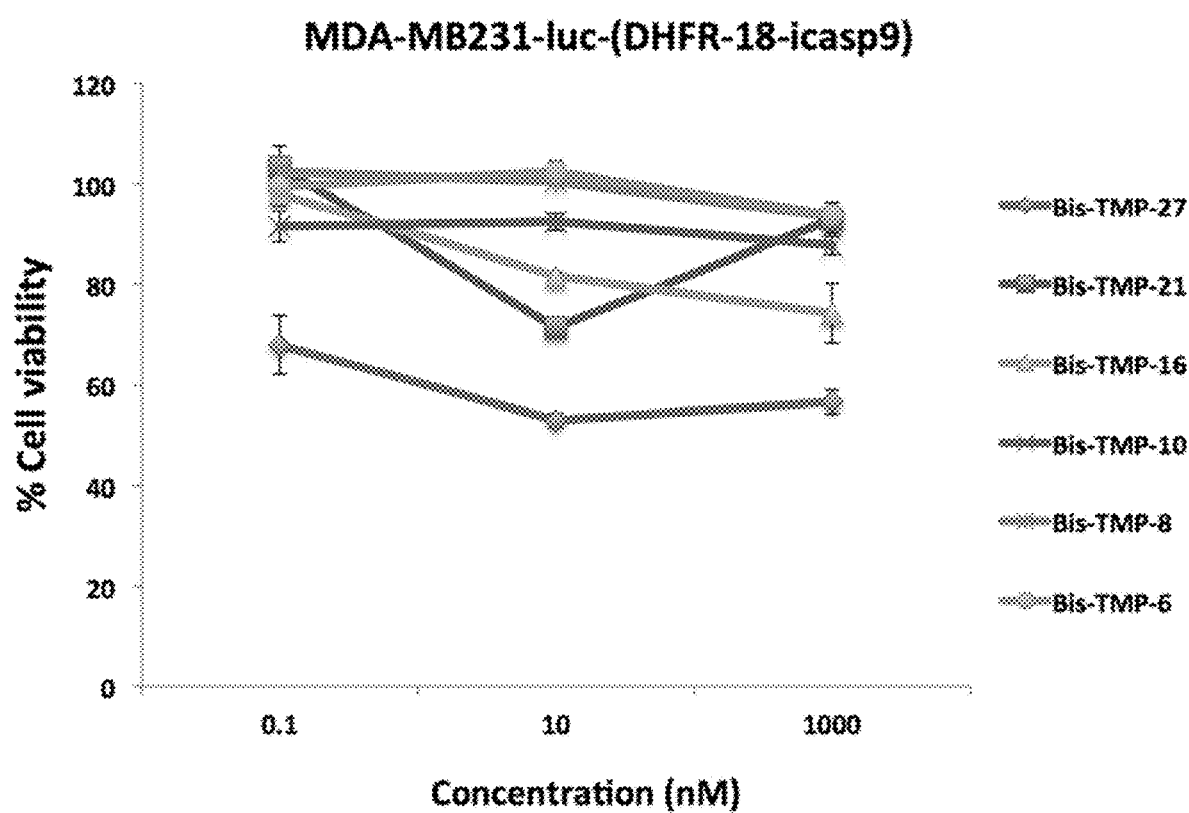

Fluoropropyl-Shield-1 (FP-Shield-1) was synthesized from the Shield-1 precursor in one step (FIG. 21). The affinity of the synthesized FP-Shield-1 for F36V-FKBP was evaluated using HCT116 cells expressing luciferase fused to the FKBP12 L106P destabilizing domain (L106P-tsLuc). HCT116 cells were treated with increasing concentrations of synthesized FP-Shield-1 or commercially available Shield-1 (from Cheminpharma, LLC), and incubated with luciferin. The results demonstrated that the affinity of FP-Shield-1 for F36V-FKBP is similar to commercially available Shield-1. Thus, [$^{18}$F]FP-Shield-1 should serve as an effective PET probe for imaging F36V-FKBP expression (including iCasp9 expression or LID expression) in vivo. Other [$^{18}$F] labeled derivatives of Shield-1 (FIGS. 10A-10B) are also expected to bind to F36V-FKBP with high affinity. [$^{18}$F] labeled derivatives of Shield-1 are expected to provide better image quality and sensitivity compared to [$^{11}$C]Shld1.

Example 5

Figure 11:
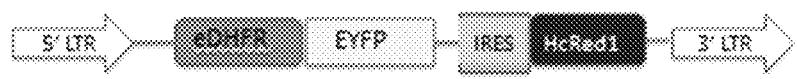
FIG. 11 is a series of diagrams illustrating the generation of pBMN-eDHFR-Casp9.
Figure 11:
Figure 11:

Development of a Modified iCasp9 Suicide Gene with eDHFR as the Ligand Binding Domain A modified iCasp9 dual function suicide-reporter gene in which the ligand binding domain (F36V-FKBP) has been replaced by eDHFR was generated (FIG. 11).

The eDHFR iCasp9 system was created by linking eDHFR to modified caspase 9 via a Ser-Gly-Gly-Gly-Ser (SEQ ID NO: 1) linker, as described in the literature for the F36V-FKBP component of the original iCasp9 system (Di Stasi et al., N Engl J Med. 2011; 365(18):1673-1683).

Figure 12:
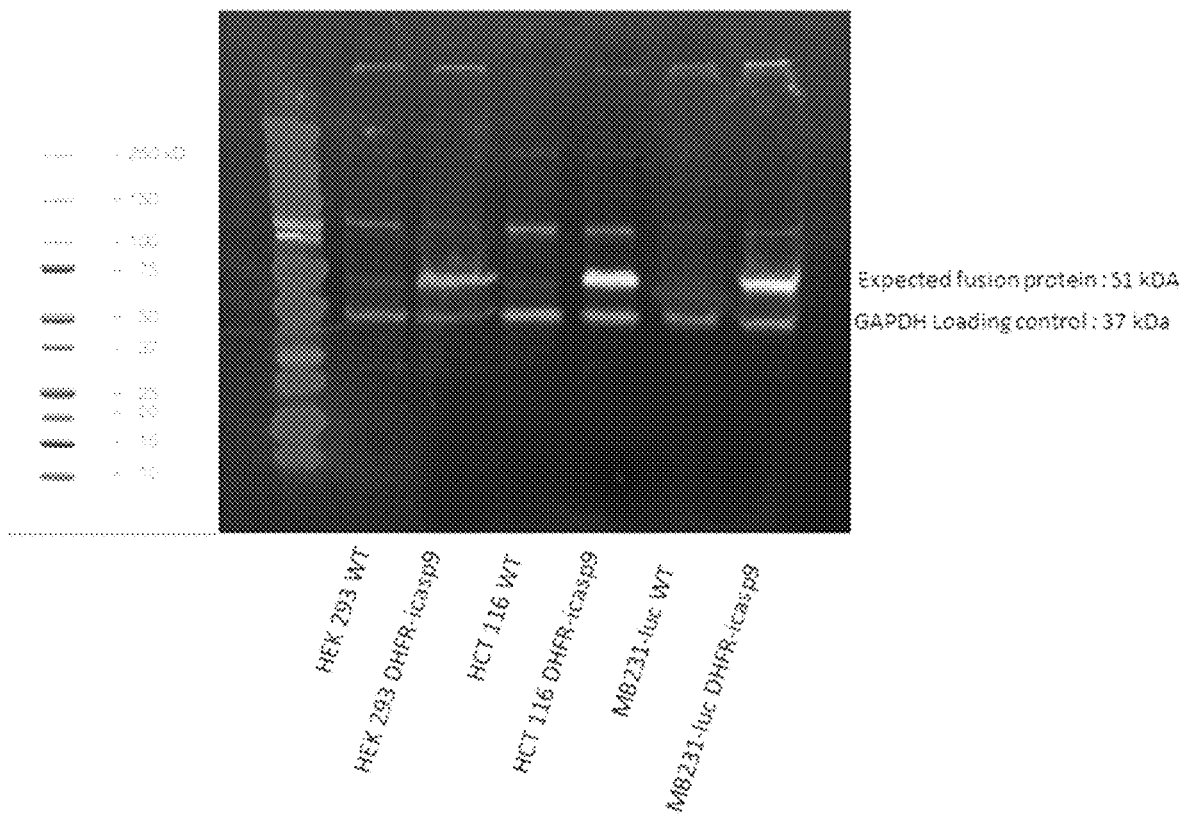
FIG. 12 is a western blot depicting the eDHFR-iCasp9 fusion protein in various cells: HEK293, HCT116 and MB231.
Figure 13:
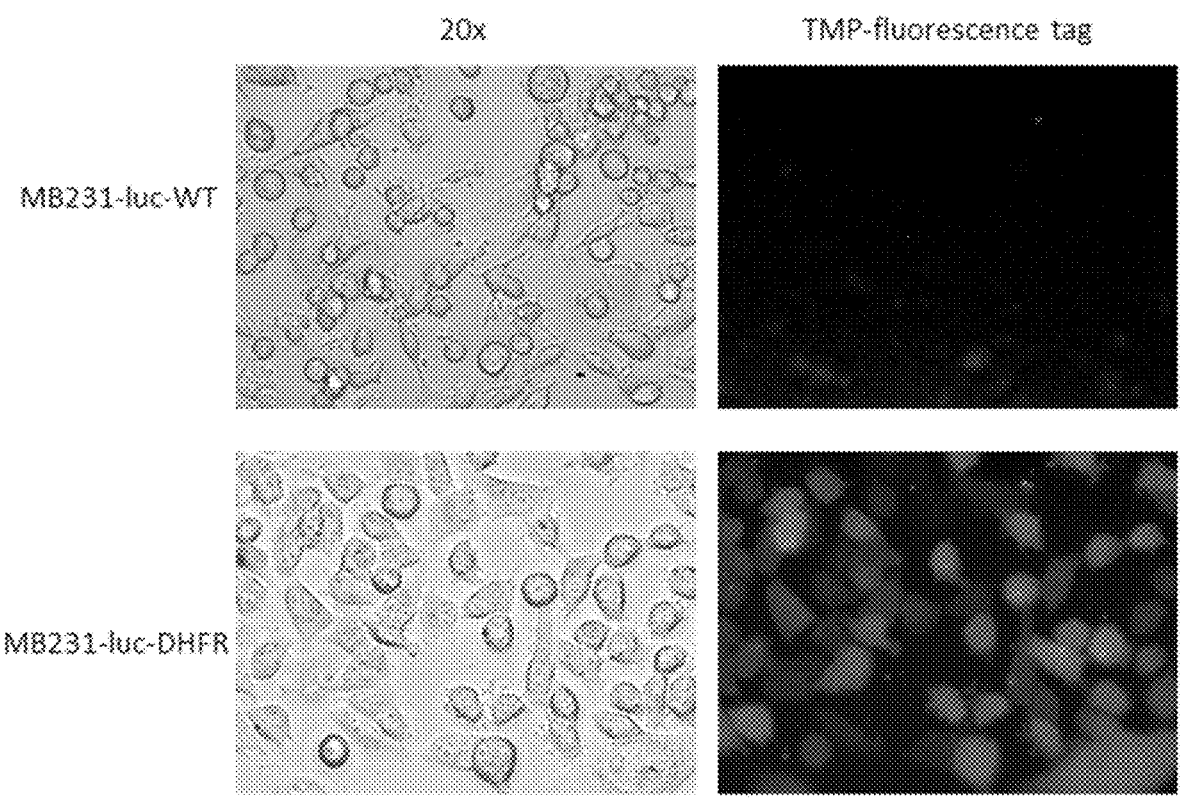
FIG. 13 is a series of images depicting the labeling of DHFR-icasp9 cells with Ligandlink (fluorescein label with TMP): WT cells do not bind to fluorescent TMP, but MB231 cells transduced with DHFR-iCasp9 do.
Figure 14:
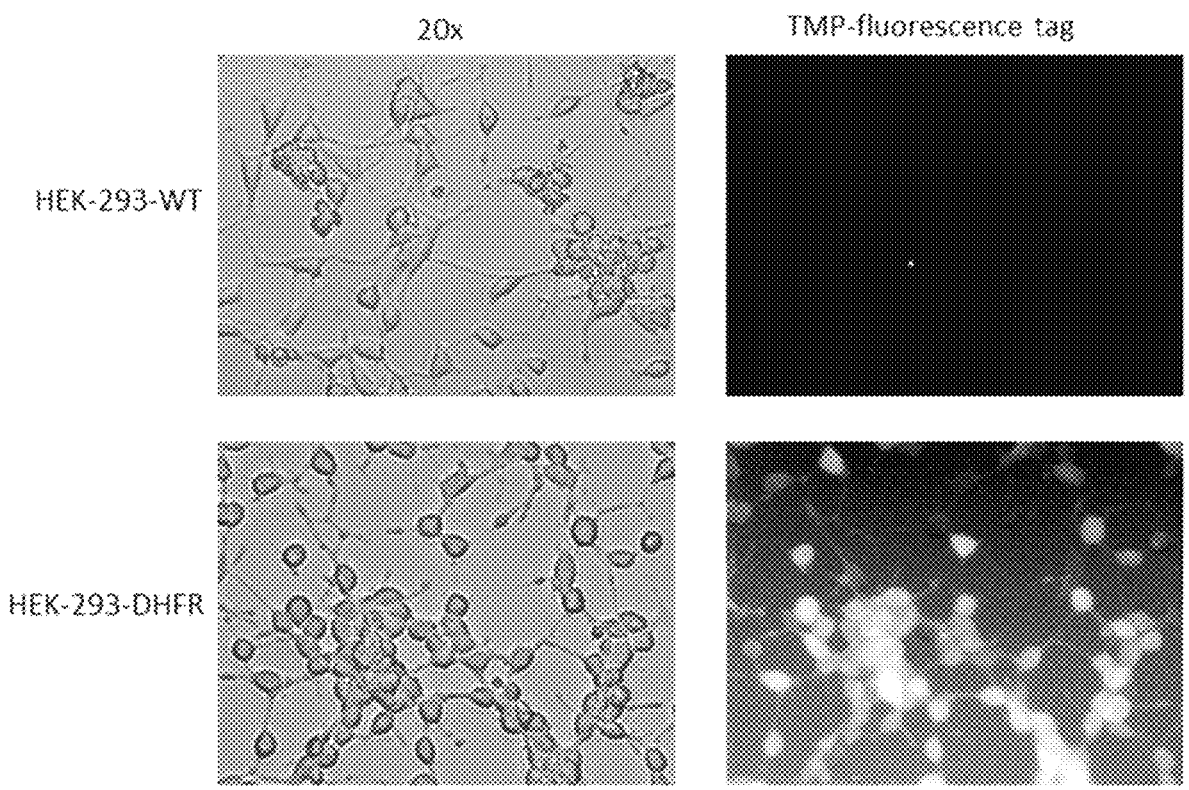
FIG. 14 is a series of images depicting the labeling of DHFR-icasp9 cells with Ligandlink (fluorescein label with TMP): WT cells do not bind to fluorescent TMP, but HEK293 cells transduced with DHFR-iCasp9 do.
Figure 15:
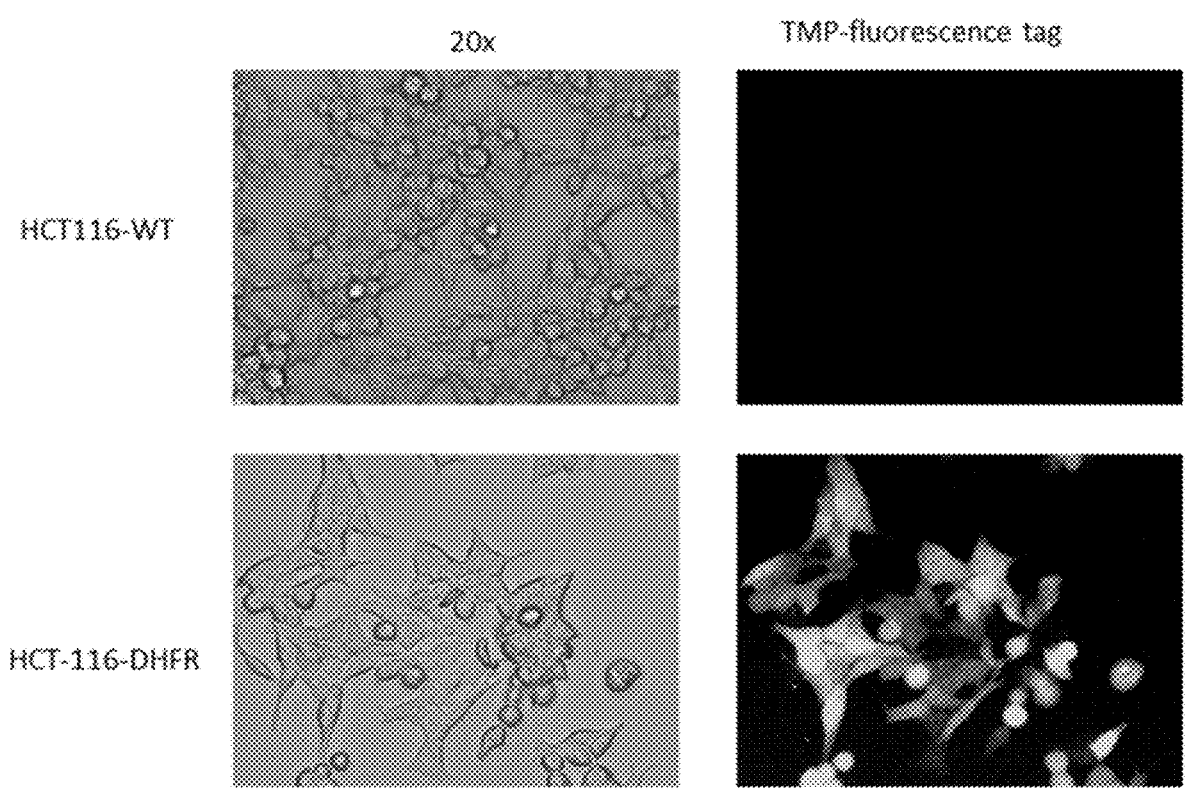
FIG. 15 is a series of images depicting the labeling of DHFR-icasp9 cells with Ligandlink (fluorescein label with TMP): WT cells do not bind to fluorescent TMP, but HCT116 cells transduced with DHFR-iCasp9 do.
Figure 16:
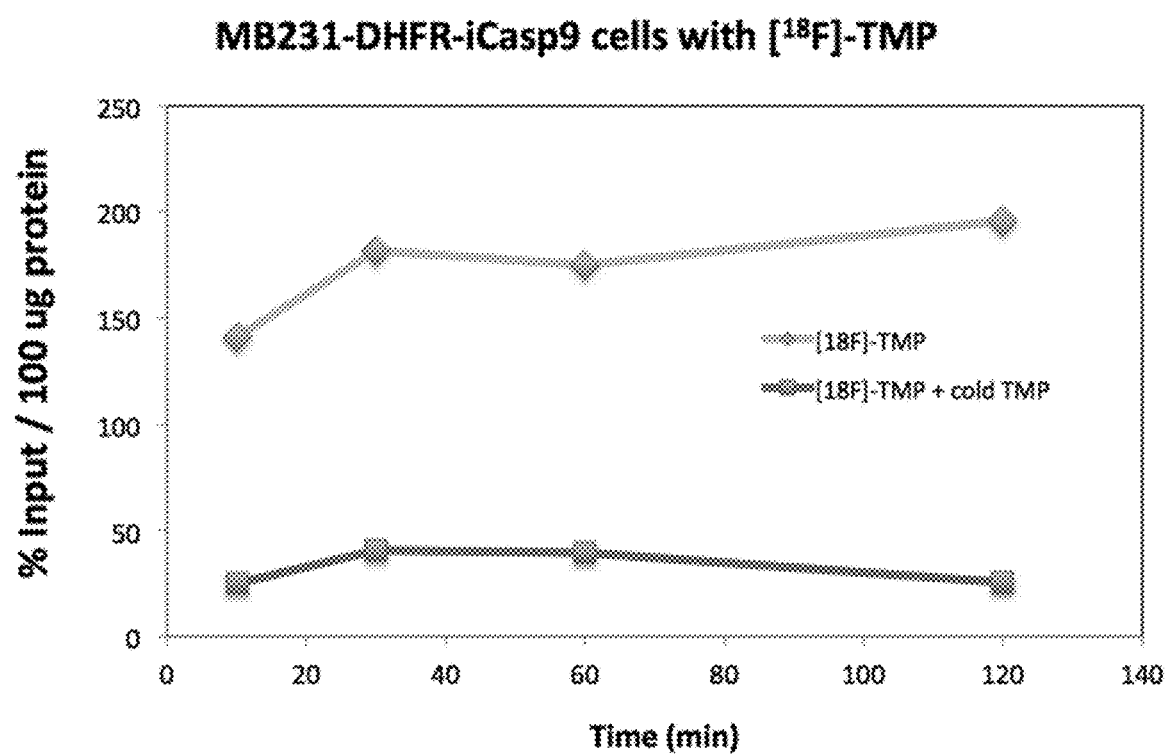
FIG. 16 is a graph illustrating a [$^{18}$F]-TMP cell uptake study. MB231 cells transduced with DHFR-iCasp9 take up [$^{18}$F]-TMP rapidly, and the uptake slightly increases over time. The uptake can be blocked by a large excess of cold TMP, thus the nonspecific binding is low.
Figure 17:
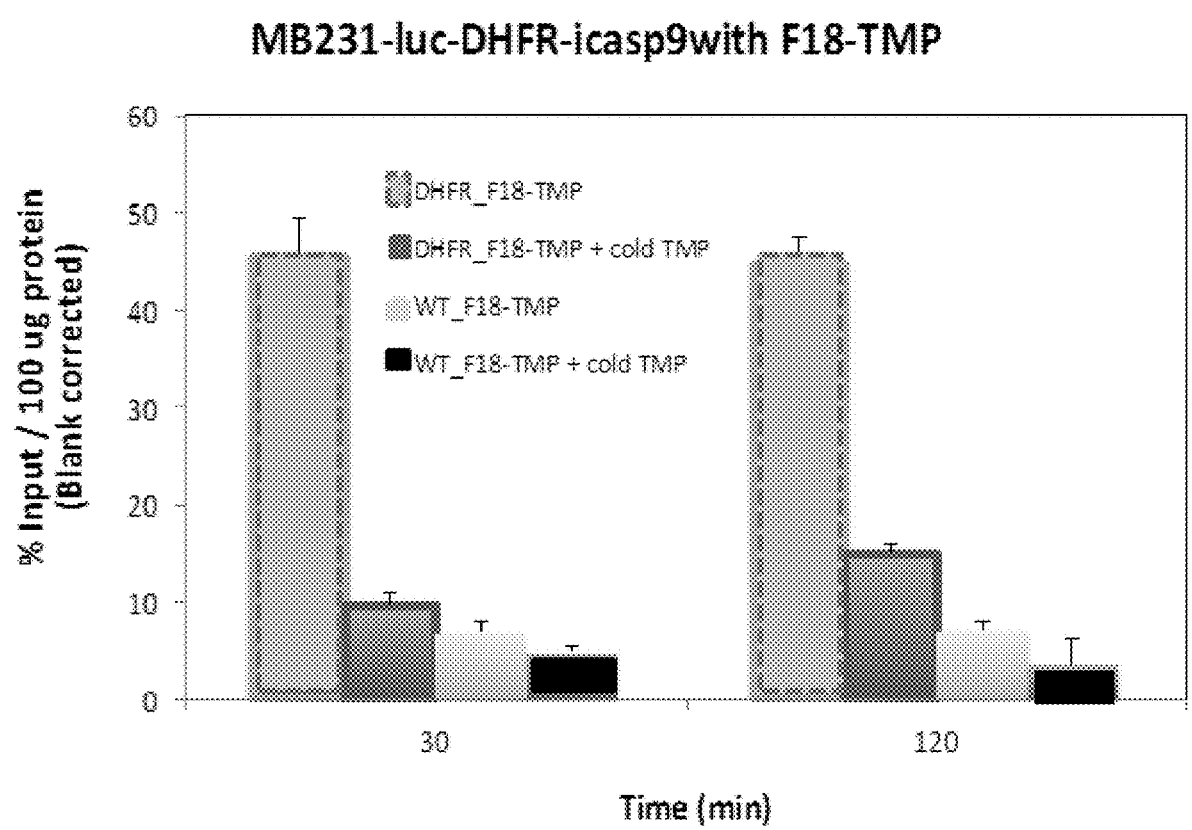
FIG. 17 is a histogram illustrating a [$^{18}$F]-TMP cell uptake study. MB231 cells transduced with DHFR-iCasp9 take up [$^{18}$F]-TMP, with similar uptake at 30 min and 120 min. The uptake can be blocked by a large excess of cold TMP, and WT cells do not take up [$^{18}$F]-TMP, thus the amount of nonspecific binding is low.
Figure 18:
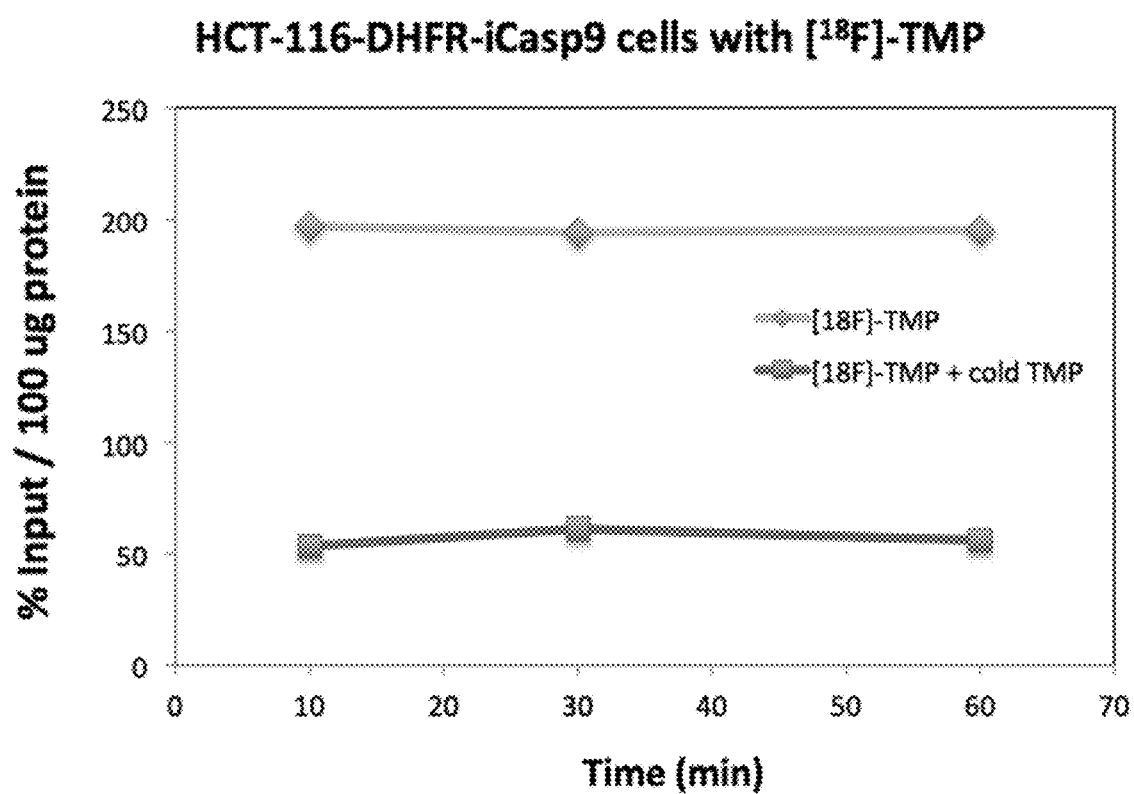
FIG. 18 is a graph illustrating a [$^{18}$F]-TMP cell uptake study. HCT116 cells transduced with DHFR-iCasp9 take up [$^{18}$F]-TMP rapidly, and the uptake is stable over time. The uptake can be blocked by a large excess of cold TMP, thus the amount of nonspecific binding is low.
Figure 19:
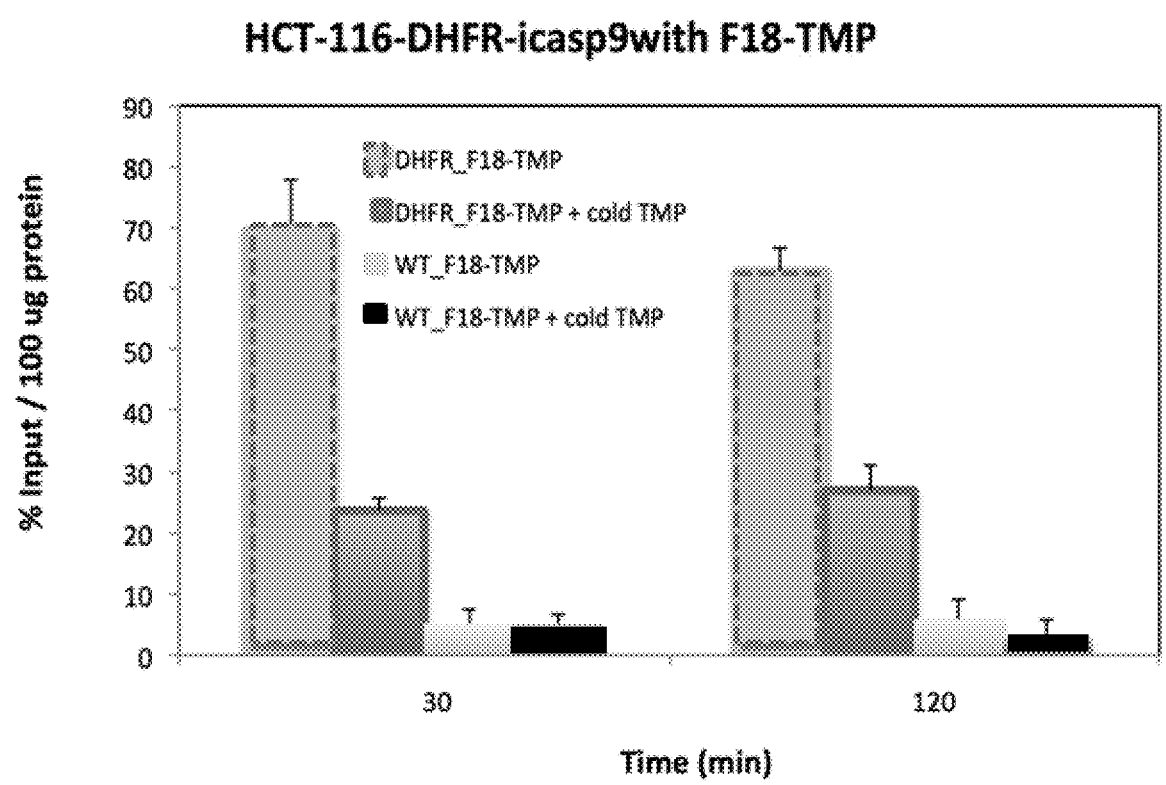
FIG. 19 is a histogram illustrating a [$^{18}$F]-TMP cell uptake study. HCT116 cells transduced with DHFR-iCasp9 take up [$^{18}$F]-TMP rapidly, with similar uptake at 30 min and 120 min. The uptake can be blocked by a large excess of cold TMP, and WT cells do not take up [$^{18}$F]-TMP, thus the amount of nonspecific binding is low.
Figure 20:
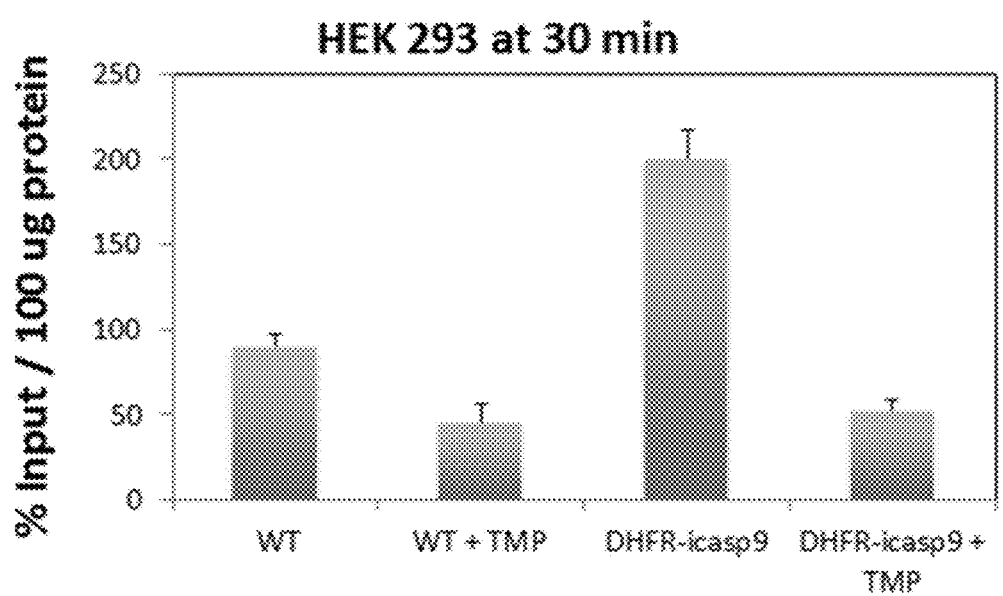
FIG. 20 is a histogram illustrating a [$^{18}$F]-TMP cell uptake study. HEK293 cells transduced with DHFR-iCasp9 take up [$^{18}$F]-TMP well at 30 min. The uptake can be blocked by a large excess of cold TMP, and WT cells do not take up [$^{18}$F]-TMP, thus the amount of nonspecific binding is low.

A western blot depicted the eDHFR-iCasp9 fusion protein in HEK293, HCT116, and MB231 cells (FIG. 12). HEK293, HCT116, and MB231 cells transduced with DHFR-iCasp9 were labeled with a Ligand-link (fluorescein linked with TMP); untransduced cells were not labeled with fluorescent TMP (FIGS. 13-15).

Cell uptake studies were performed with [$^{18}$F]TMP in cells transduced with eDHFR iCasp9, in a similar manner as described for [$^{11}$C]Shld1. [$^{18}$F]TMP was taken up rapidly by MB231, HCT116, and HEK293 cells transduced with eDHFR iCasp9 (FIGS. 16-20). The uptake could be blocked by a large excess of cold TMP, consistent with low nonspecific binding; untransduced cells were also used as a control.

Example 6

Development of a Functional DHFR-iCasp9 Suicide Gene, and Synthesis of a Library of Bis-TMP Compounds with Varying Linker Lengths A library of Bis-TMP compounds was synthesized in which the linker between TMP molecules was 6, 8, 10, 16, 21, 27, or 33 atoms in length (FIG. 25). A Tris-TMP was also synthesized (FIG. 25).

Various DHFR-iCasp9 constructs were created in which the linker between DHFR and iCasp9 was modified to be 5, 6, 9, 15, or 18 amino acids in length. The percentage viability of MDA-MB231 cells transduced with these DHFR-iCasp9 constructs was then assessed following treatment with a variety of Bis-TMP compounds at increasing concentrations (FIGS. 23A-23F). Wild-type MDA-MB231 cells were also evaluated as a control. Most combinations did not produce any cell killing; only DHFR-iCasp9 linkers of 15 or 18 amino acids, and Bis-TMP linkers of 21 and 27 atoms demonstrated cell killing.

Figure 24A:
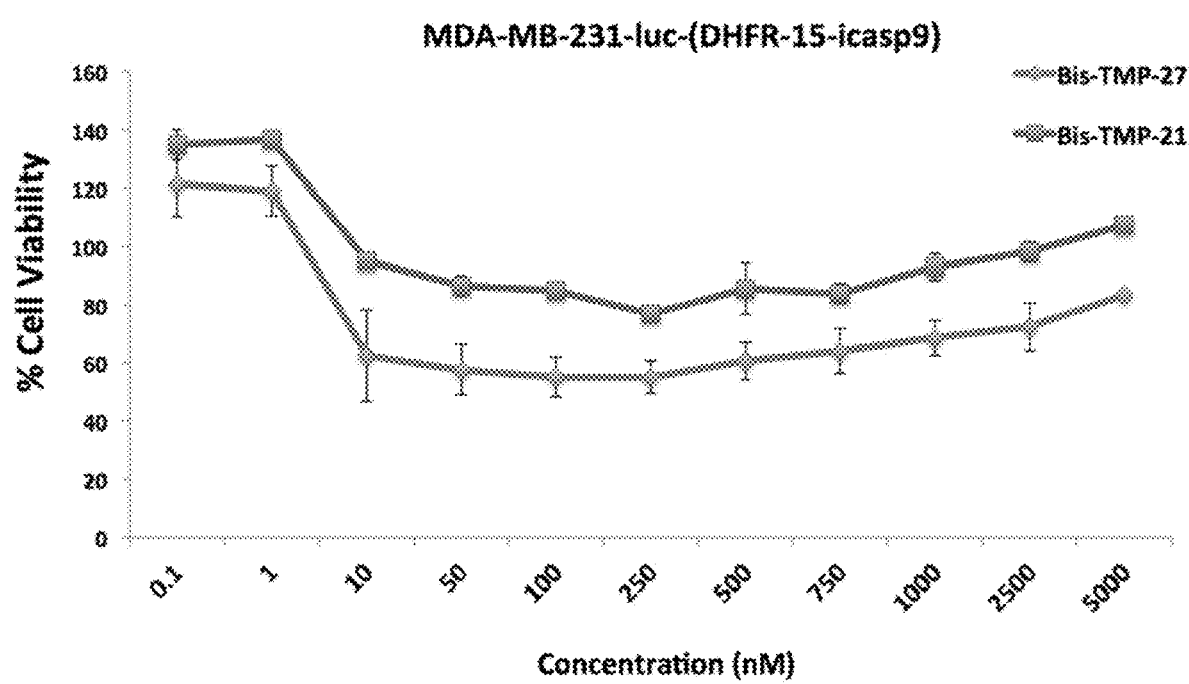
FIGS. 24A-24B are a series of graphs depicting the % viability of MDA-MB231 cells that have been transduced with DHFR-15-iCasp9 or DHFR-18-iCasp9 (with 15 or 18 amino acid linkers, respectively) and treated with Bis-TMP-21 or Bis-TMP-27 (with 21 or 27 atoms linkers, respectively) at increasing concentrations. The graphs illustrate potent activation of the DHFR-iCasp9 suicide gene at low nM concentrations of Bis-TMP. The DHFR-18-iCasp9 suicide gene and Bis-TMP-27 were the most effective combination, killing ~70% of cells with an IC$_{50}$ of ~5 nM.
Figure 24B:
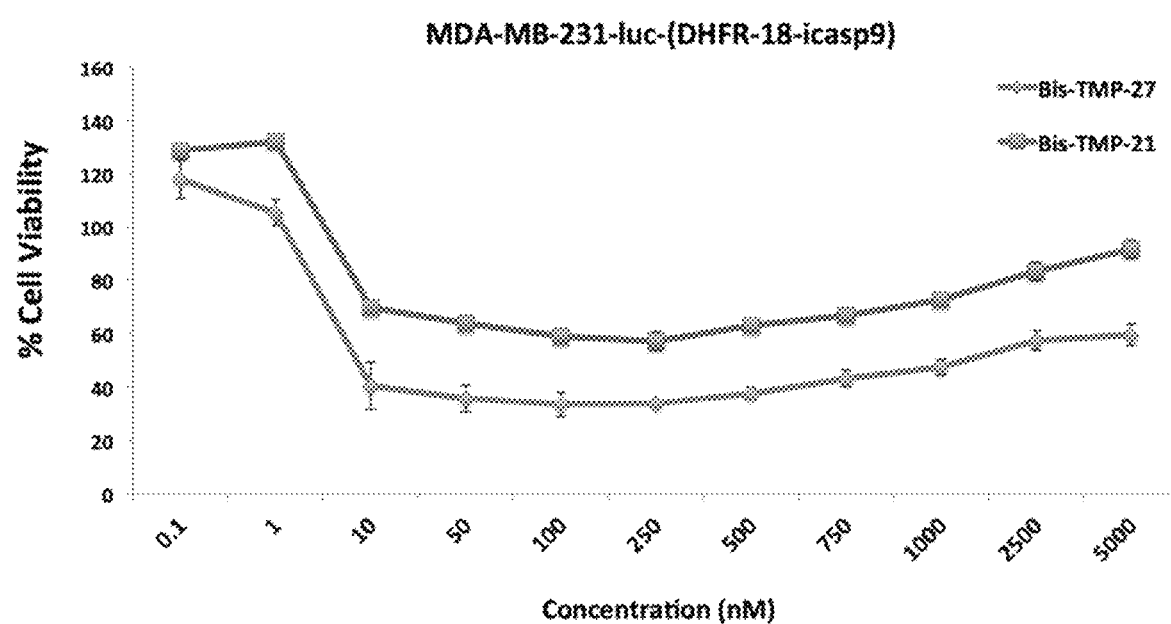
Figure 25A:
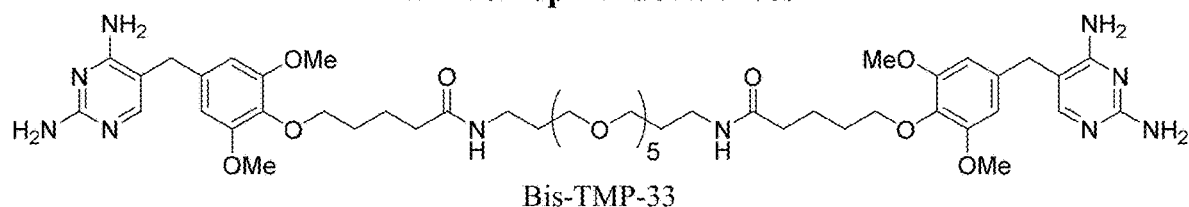
FIGS. 25A-25B are a series of chemical structures depicting all of the Trimethoprim (TMP) compounds of the present invention. Bis-TMP=bis-trimethoprim and Tris-TMP=tris-trimethoprim.
Figure 25A:
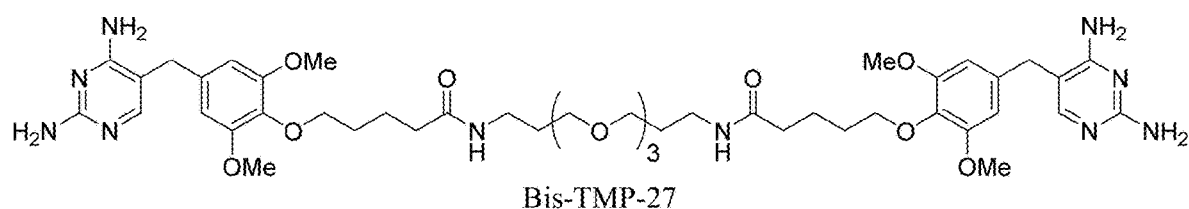
Figure 25A:
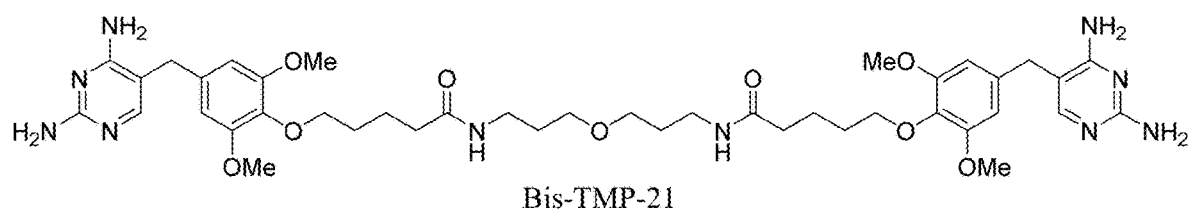
Figure 25A:
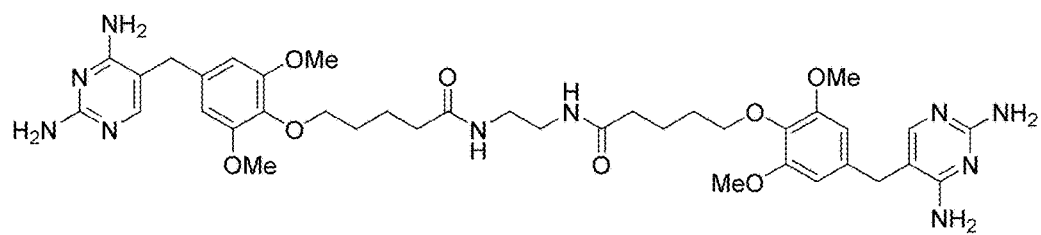
Figure 25B:
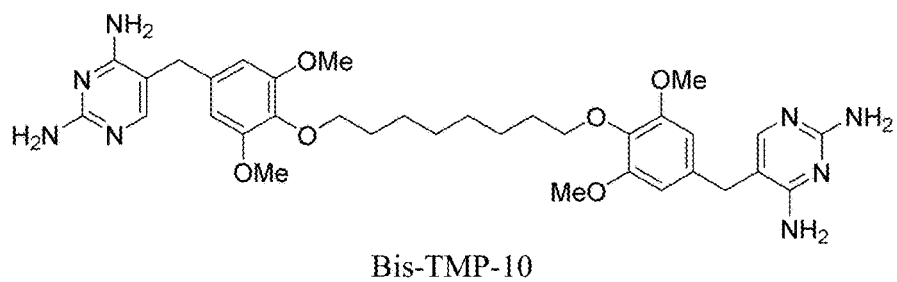
Figure 25B:
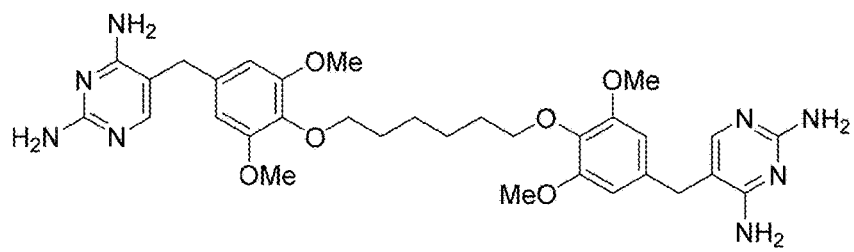
Figure 25B:
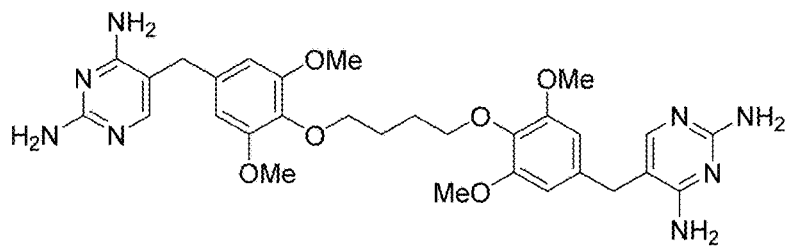
Figure 25B:
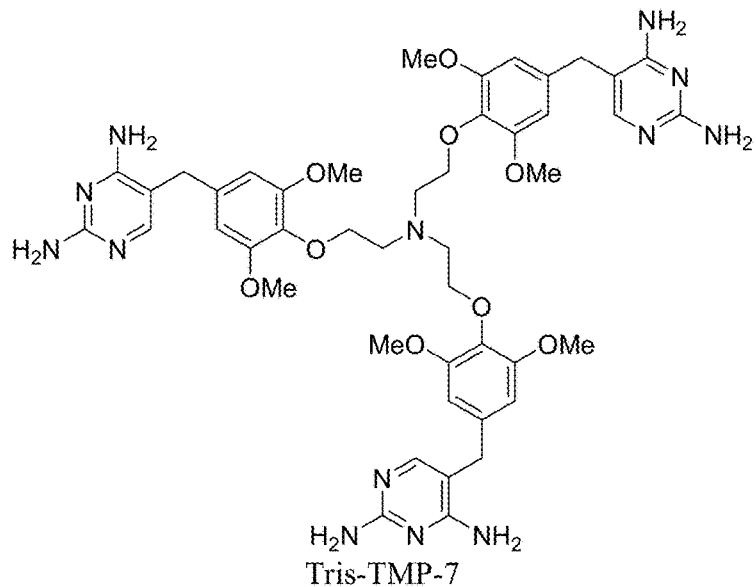

A more detailed analysis of the percentage (%) viability of MDA-MB231 cells transduced with DHFR-15-iCasp9 or DHFR-18-iCasp9 (with 15 or 18 amino acid linkers, respectively) was then assessed following treatment with Bis-TMP-21 or Bis-TMP-27 (with 21 or 27 atoms linkers, respectively) at increasing concentrations (FIGS. 24A-24B). These graphs illustrate potent activation of the DHFR-iCasp9 suicide gene at low nM concentrations of Bis-TMP. The DHFR-18-iCasp9 suicide gene and Bis-TMP-27 were the most effective combination, killing ~70% of cells with an $IC_{50}$ of ~5 nM (FIG. 24B).

Example 7

Application

Further to the disclosure elsewhere herein, this invention includes the first dual function reporter gene, based on iCasp9, that serves as both a PET imaging reporter gene and a suicide gene. Although imaging reporter genes and potent suicide genes both exist, an imaging reporter gene (much less a dual function reporter gene) that is acceptable for routine clinical use has thus far not been contemplated. The invention fills a void in the clinical research toolbox by creating an imaging reporter gene that is acceptable for routine clinical use, in part because it has a potent safety switch. Since CAR T cells therapy and other gene therapies carry significant risk, the elegance of a dual function suicide-reporter is key from both a regulatory and patient perspective. Also, one aspect of this invention includes a modified iCasp9, in which the ligand binding domain has been replaced with eDHFR, and is capable of being imaged with [$^{18}$F]TMP.

The present invention includes a dual function reporter gene that has the potential to find widespread use in CAR T cell therapy and other cell-based therapies as both a PET imaging reporter gene and a suicide gene. The invention provides methods for biodistribution and patterns of trafficking of CAR T cells, provides insight into the mechanism of action of CAR T cell therapy, including an assessment of therapy-related toxicities, and helps in the design of more effective T cell therapies (and other cell-based therapies) for cancer. The imaging tools of this invention can be used routinely in the clinic to answer questions about response and therapy-related toxicities, and the presence of a potent suicide gene serves as a valuable safety switch which could be employed to control the many toxicities that are inherent in CAR T cell therapy (such as cytokine release syndrome, neurological toxicity, on-target/off-tumor toxicity, insertional oncogenesis, graft versus host disease, and off-target antigen recognition).

OTHER EMBODIMENTS

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition comprising a ligand of F36V-FKBP of formula (II):

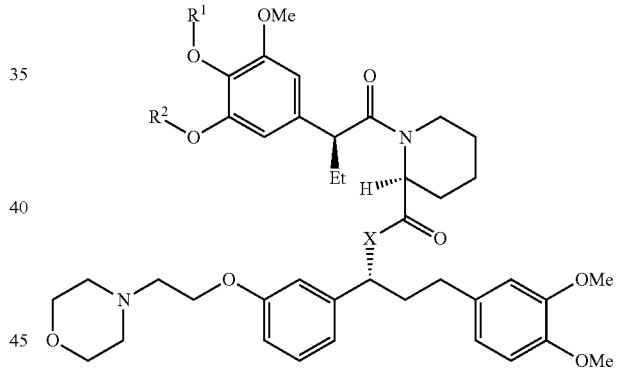

wherein
X is NH or O;
a) $R^1$ is $CH_2Y$, $CH_2CH_2Y$, or $CH_2CH_2CH_2Y$ and $R^2$ is $CH_3$; or
b) $R^2$ is $CH_2Y$, $CH_2CH_2Y$, or $CH_2CH_2CH_2Y$ and $R^1$ is $CH_3$; and
Y is F or $^{18}F$.

* * * * *

SEQUENCE LISTING

```
<160> NUMBER OF SEQ ID NOS: 1

<210> SEQ ID NO 1
<211> LENGTH: 5
<212> TYPE: PRT
<213> ORGANISM: Artificial Sequence
<220> FEATURE:
<223> OTHER INFORMATION: Artificially synthesized

<400> SEQUENCE: 1

Ser Gly Gly Gly Ser
1               5
```